US010809538B2

(12) United States Patent
Koyama et al.

(10) Patent No.: US 10,809,538 B2
(45) Date of Patent: Oct. 20, 2020

(54) IMAGE ACQUISITION APPARATUS, SPECTRAL APPARATUS, METHODS, AND STORAGE MEDIUM FOR USE WITH SAME

(71) Applicant: CANON U.S.A., INC., Melville, NY (US)

(72) Inventors: Osamu Koyama, Tokyo (JP); Akira Yamamoto, Saitama (JP); Naoki Kohara, Kawasaki (JP)

(73) Assignee: Canon U.S.A., Inc., Melville, NY (US)

( * ) Notice: Subject to any disclaimer, the term of this patent is extended or adjusted under 35 U.S.C. 154(b) by 117 days.

(21) Appl. No.: 15/823,441

(22) Filed: Nov. 27, 2017

(65) Prior Publication Data

US 2019/0162977 A1 May 30, 2019

(51) Int. Cl.
*G01B 9/02* (2006.01)
*G02B 27/10* (2006.01)
(Continued)

(52) U.S. Cl.
CPC ........ *G02B 27/1013* (2013.01); *A61B 5/0075* (2013.01); *A61B 5/6852* (2013.01);
(Continued)

(58) Field of Classification Search
CPC .... G02B 27/1013; G02B 6/0068; G02B 6/34; G02B 6/3624; G02B 6/4215;
(Continued)

(56) References Cited

U.S. PATENT DOCUMENTS 4,965,441 A 10/1990 Picard
6,341,036 B1 1/2002 Tearney et al.
(Continued)

FOREIGN PATENT DOCUMENTS

JP 05-157628 A 6/1993
JP 1993157628 A 6/1993
(Continued)

OTHER PUBLICATIONS

Yelin, D., et al., "Three-dimensional miniature endoscopy", Nature, Oct. 19, 2006, pp. 765, vol. 443.
(Continued)

*Primary Examiner* — Tarifur R Chowdhury
*Assistant Examiner* — Jonathon Cook
(74) *Attorney, Agent, or Firm* — Canon U.S.A., Inc. I.P. Division

(57) ABSTRACT

Image acquisition apparatuses, spectral apparatuses, methods and storage mediums for use with same are provided herein. At least one apparatus includes: a diffraction element irradiated by a light; a fiber for receiving reflected scattered light from a subject; a diffraction grating dispersing the transmitted light into light fluxes of wavelength bands again; an optical system imaging the split light fluxes; and an imaging device near the focal point of the optical system. An image is changed by rotating the diffraction grating, from which a two-dimensional image is acquired. The transmitted light may be branched into two or more, and input to a collimator lens and imaged as multiple spectral sequences by the optical system. At least one apparatus may form light fluxes traveling at different angles; and may acquire spectral information of the reflected and scattered light. Preferably, for the luminous fluxes, no gap exists in an image.

21 Claims, 36 Drawing Sheets

(51) Int. Cl.
*F21K 9/64* (2016.01)
*F21V 8/00* (2006.01)
*G01J 3/50* (2006.01)
*G01J 3/02* (2006.01)
*G01J 3/04* (2006.01)
*G01J 3/28* (2006.01)
*A61B 5/00* (2006.01)
*G01J 3/36* (2006.01)
*G01J 3/18* (2006.01)
*G02B 6/42* (2006.01)
*G02B 6/36* (2006.01)
*G02B 6/34* (2006.01)

(52) U.S. Cl.
CPC .............. *F21K 9/64* (2016.08); *G01J 3/024* (2013.01); *G01J 3/0208* (2013.01); *G01J 3/0218* (2013.01); *G01J 3/04* (2013.01); *G01J 3/18* (2013.01); *G01J 3/2823* (2013.01); *G01J 3/36* (2013.01); *G01J 3/502* (2013.01); *G02B 6/0068* (2013.01); *A61B 5/42* (2013.01); *G02B 6/34* (2013.01); *G02B 6/3624* (2013.01); *G02B 6/4215* (2013.01); *G02B 6/4298* (2013.01)

(58) Field of Classification Search
CPC ..... G02B 6/4298; F21K 9/64; A61B 1/00064; A61B 1/00165; A61B 1/00167; A61B 5/0075; A61B 5/6852; A61B 5/42; G01J 3/0208; G01J 3/0218; G01J 3/024; G01J 3/04; G01J 3/18; G01J 3/2823; G01J 3/36; G01J 3/502
See application file for complete search history.

(56) References Cited

U.S. PATENT DOCUMENTS

| | | | |
|---|---|---|---|
| 7,447,408 B2 | 11/2008 | Bouma et al. | |
| 7,551,293 B2 | 6/2009 | Yelin et al. | |
| 7,796,270 B2 | 9/2010 | Yelin et al. | |
| 7,847,949 B2 | 12/2010 | Tearney et al. | |
| 7,859,679 B2 | 12/2010 | Bouma et al. | |
| 7,889,348 B2 | 2/2011 | Tearney et al. | |
| 8,045,177 B2 | 10/2011 | Tearney et al. | |
| 8,145,018 B2 | 3/2012 | Shishkov et al. | |
| 8,838,213 B2 | 9/2014 | Tearney et al. | |
| 8,917,390 B2 | 12/2014 | Behr et al. | |
| 9,254,089 B2 | 2/2016 | Tearney et al. | |
| 9,295,391 B1 | 3/2016 | Tearney et al. | |
| 9,415,550 B2 | 8/2016 | Tearney et al. | |
| 9,557,154 B2 | 1/2017 | Tearney et al. | |
| 2001/0021018 A1* | 9/2001 | Basiji | G01J 3/2803 356/326 |
| 2008/0013960 A1* | 1/2008 | Tearney | A61B 1/07 398/139 |
| 2012/0101374 A1 | 4/2012 | Tearney et al. | |
| 2014/0354802 A1 | 12/2014 | Ohtomo et al. | |
| 2015/0116705 A1* | 4/2015 | Harmsma | G01J 3/02 356/300 |
| 2016/0206184 A1 | 7/2016 | Tearney et al. | |
| 2016/0341951 A1 | 11/2016 | Tearney et al. | |
| 2016/0349417 A1 | 12/2016 | Tearney et al. | |
| 2017/0035281 A1* | 2/2017 | Takeuchi | G02B 27/4227 |
| 2017/0167861 A1 | 6/2017 | Chen et al. | |
| 2017/0168232 A1 | 6/2017 | Tearney et al. | |
| 2017/0176736 A1 | 6/2017 | Yamamoto et al. | |
| 2017/0290492 A1 | 10/2017 | Hamm et al. | |
| 2017/0322079 A1 | 11/2017 | Do et al. | |
| 2018/0017778 A1 | 1/2018 | Ikuta et al. | |
| 2018/0364154 A1* | 12/2018 | Wu | G01N 21/31 |
| 2019/0104941 A1* | 4/2019 | Yamamoto | A61B 1/00172 |
| 2019/0150720 A1* | 5/2019 | Altshuler | A61B 5/7203 |

FOREIGN PATENT DOCUMENTS

| | | |
|---|---|---|
| JP | 1994233198 A | 8/1994 |
| JP | 9-172568 A | 6/1997 |
| JP | 2011023203 A | 2/2011 |
| WO | 2015/116939 A1 | 8/2015 |
| WO | 2015/116951 A2 | 8/2015 |
| WO | 2017/024145 A1 | 2/2017 |
| WO | 2017/117203 A1 | 7/2017 |
| WO | 2017/139657 A1 | 8/2017 |
| WO | 2017/165511 A1 | 9/2017 |

OTHER PUBLICATIONS

Kang, D., et al., "Spectrally-encoded color imaging", Optics Express, Aug. 17, 2009, pp. 15239-15247, vol. 17, No. 17.

Kang, D., et al., "Minature grating for spectrally-encoded endoscopy", Lab Chip, Feb. 35, 2013, pp. 1810-1816, vol. 13.

Zeidan, A., et al., "Miniature forward-viewing spectrally encoded endoscopic probe", Optics Letters, Aug. 15, 2014, pp. 4871-4874, vol. 39, Issue 16.

* cited by examiner

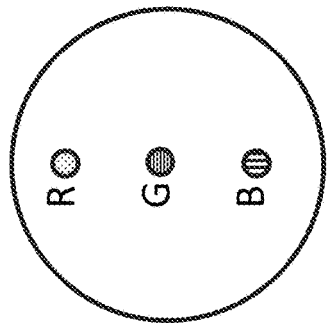
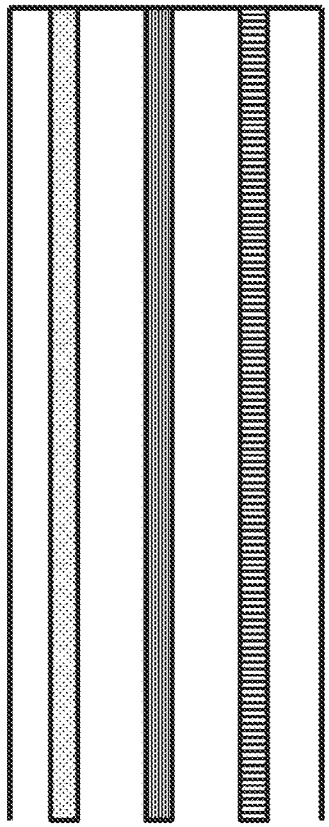
FIG. 2
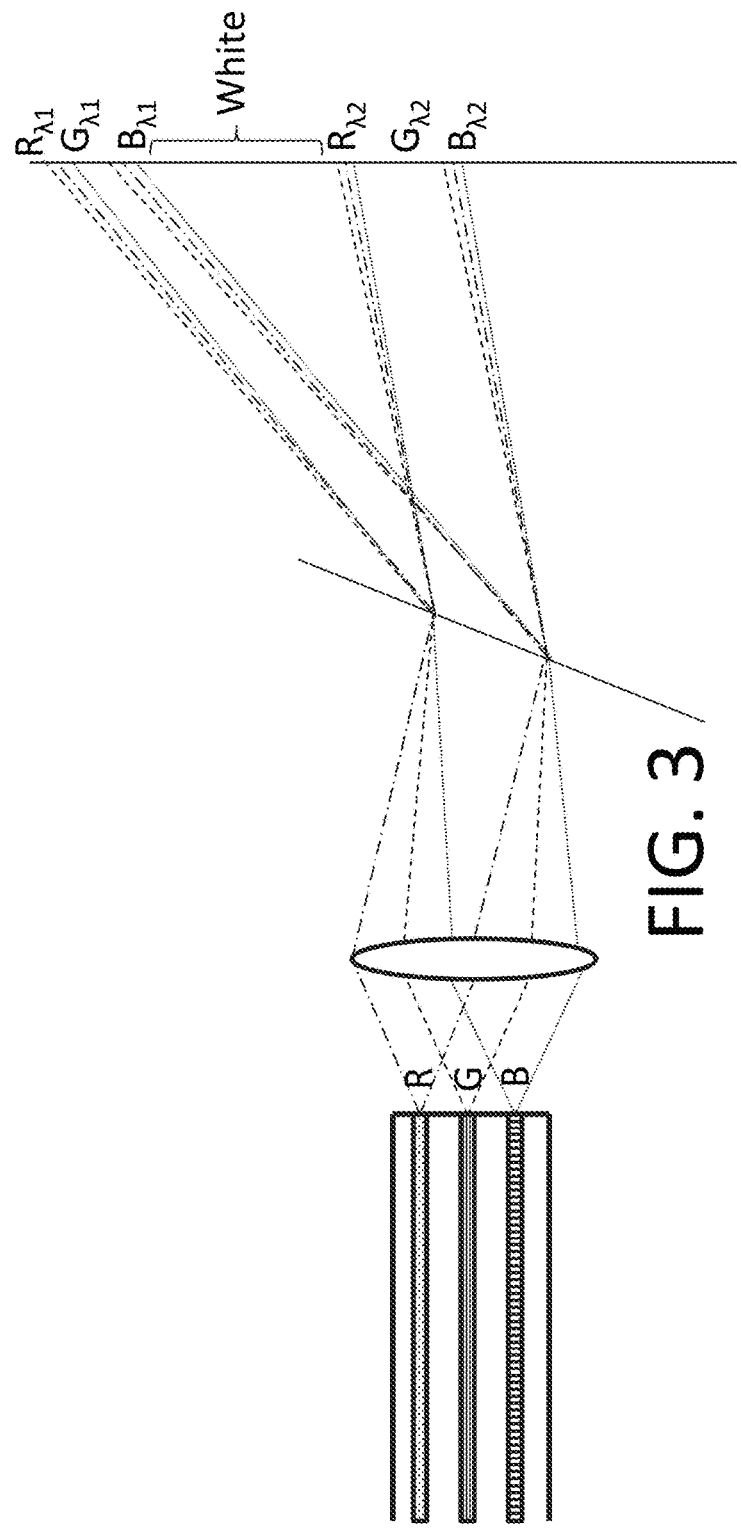
FIG. 3

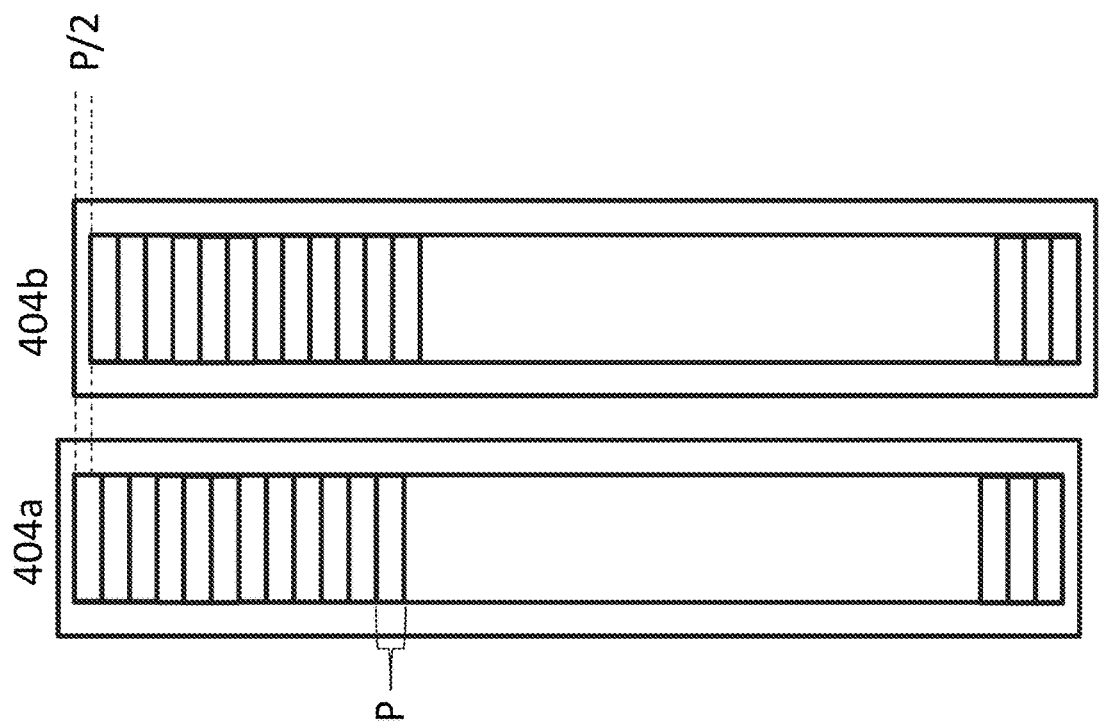

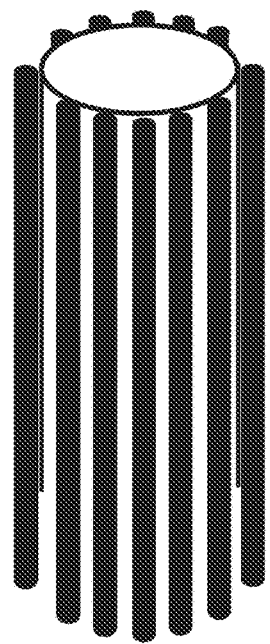
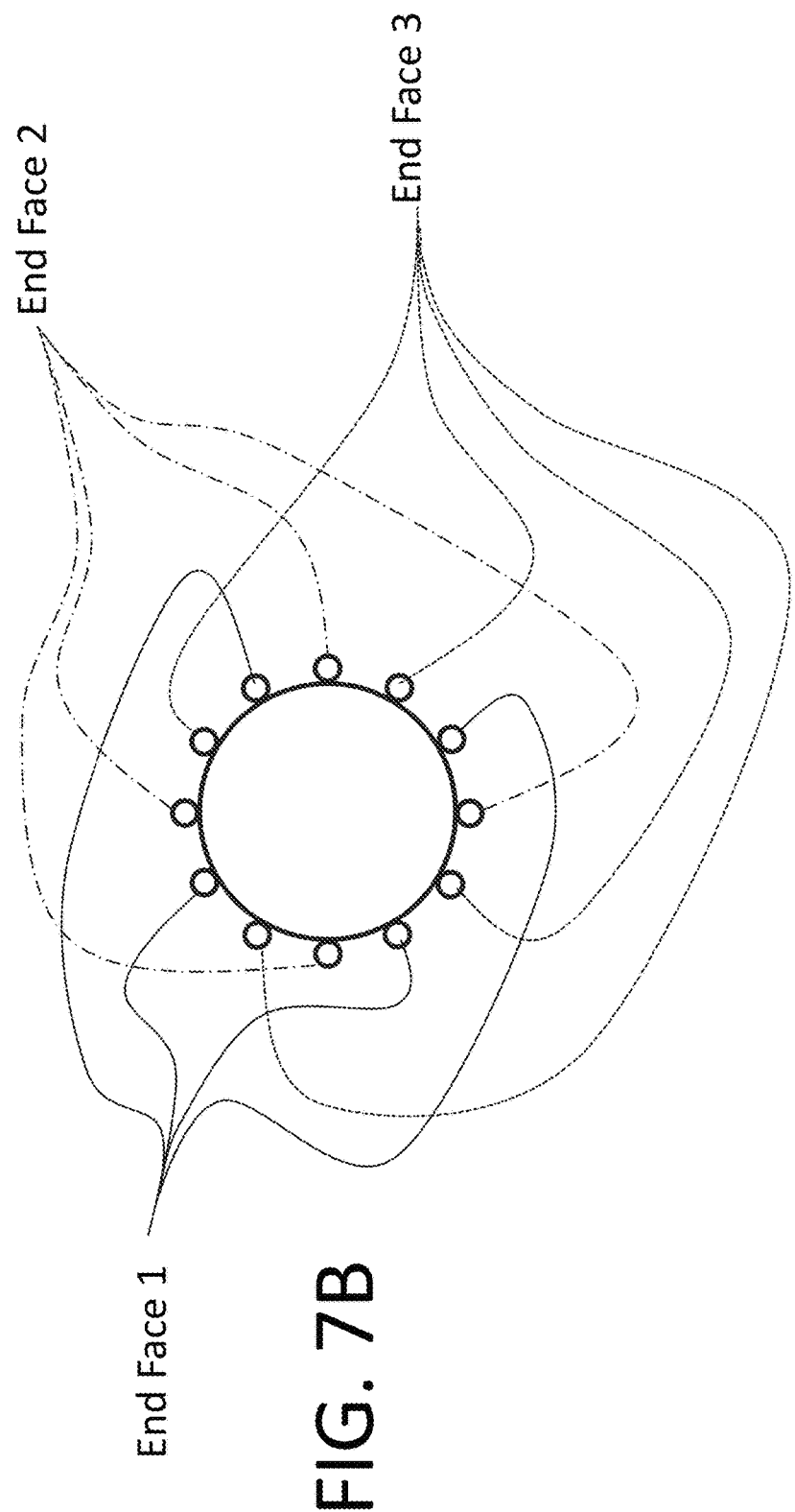
FIG. 7A
FIG. 7B

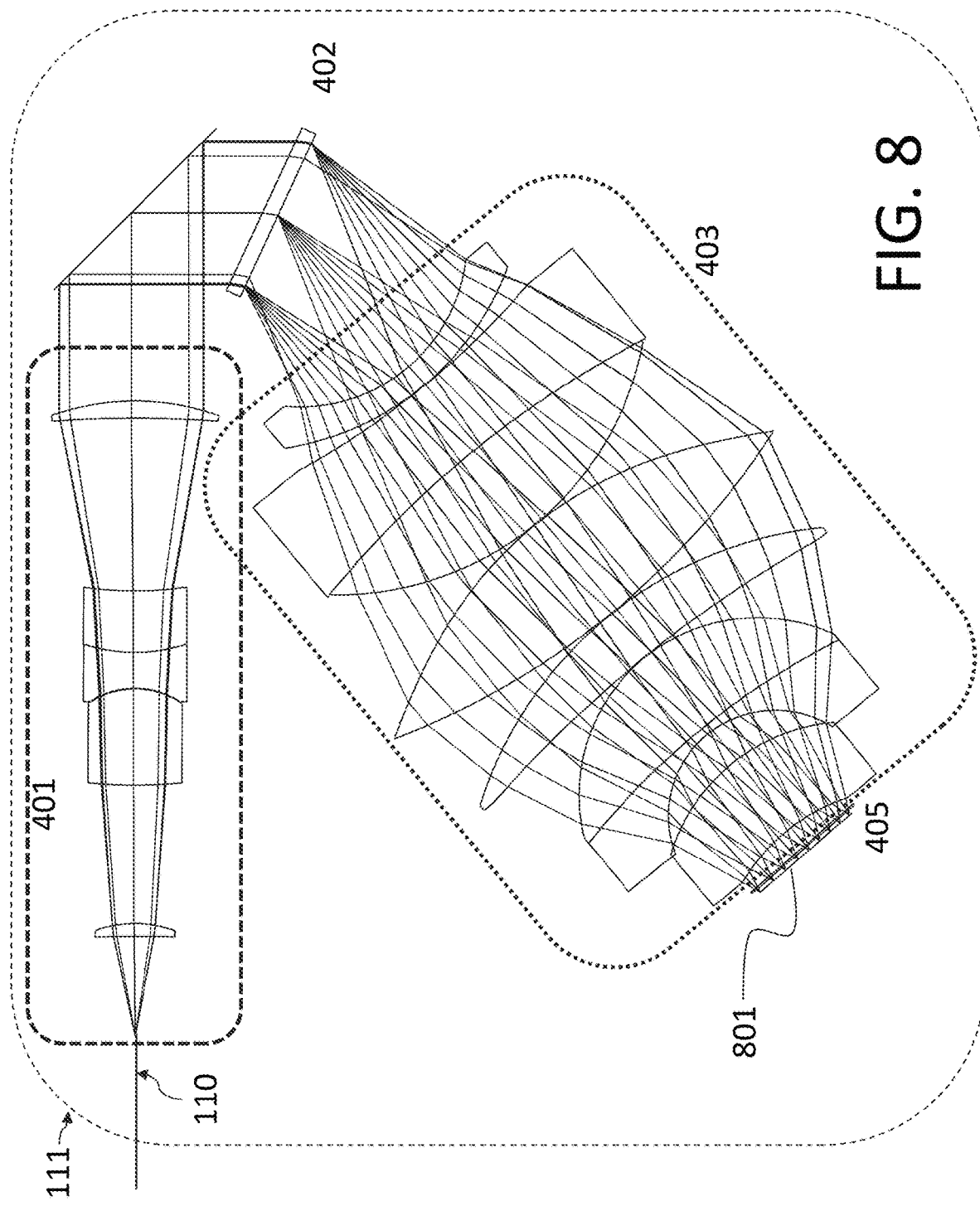

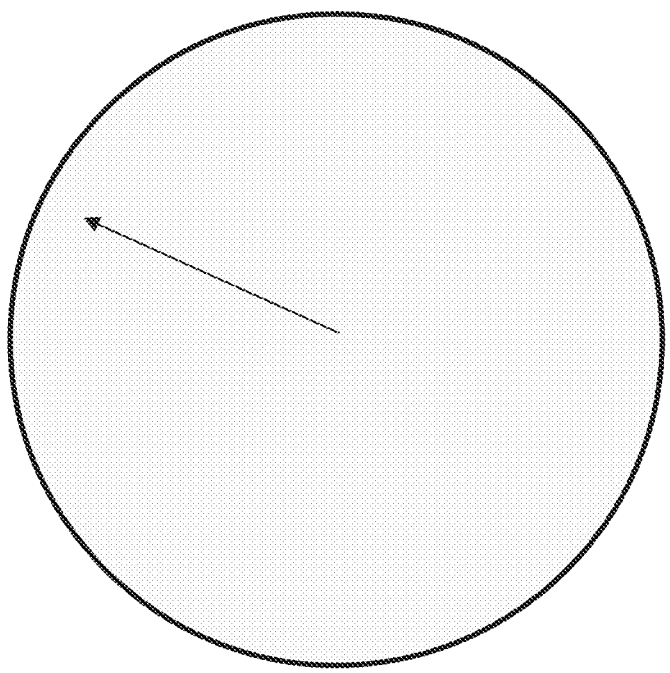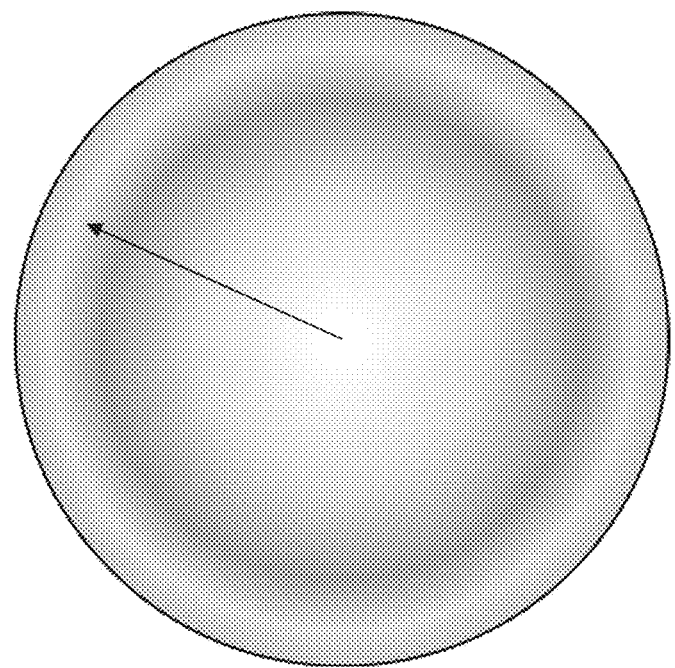
FIG. 12

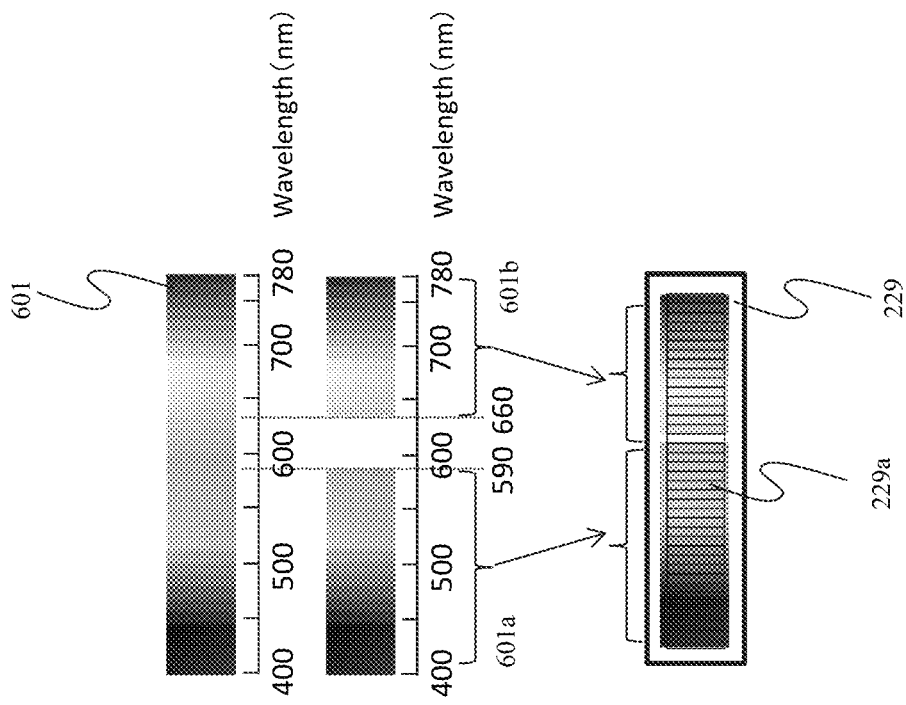

IMAGE ACQUISITION APPARATUS, SPECTRAL APPARATUS, METHODS, AND STORAGE MEDIUM FOR USE WITH SAME

BACKGROUND OF THE INVENTION

Field of the Invention

The present invention relates to one or more embodiments of an image acquisition apparatus, such as an endoscope, and a spectral apparatus, and more particularly relates to a spectroscope that splits and measures obtained light fluxes according to wavelengths, such as, but not limited to, spectrally encoded endoscopy (SEE) apparatuses and systems, and methods and storage mediums for use with same. Examples of SEE applications include imaging, evaluating and characterizing/identifying biological objects or tissue, such as, but not limited to, for gastro-intestinal, cardio and/or ophthalmic applications.

Description of the Related Art

There have been known endoscope apparatuses used for intraluminal measurement. Endoscopes enable real-time observation of intraluminal information. The smaller the outer diameter is, the wider the variety of lumina into which the endoscope can be inserted is, which may increase the observation area.

Spectrally encoded endoscope (SEE) is an endoscope technology which uses a broadband light source, a rotating grating and a spectroscopic detector to encode spatial information on a sample. When illuminating light to the sample, the light is spectrally dispersed along one illumination line, such that the dispersed light illuminates a specific position of the illumination line with a specific wavelength. When the reflected light from the sample is detected with the spectrometer, the intensity distribution is analyzed as the reflectance along the line. By rotating or swinging the grating back and forth to scan the illumination line, a two-dimensional image of the sample is obtained.

One example of a small-diameter endoscope is a wavelength-encoding endoscope such as in U.S. Pat. No. 6,341,036. The SEE device described in U.S. Pat. No. 6,341,036 inputs white light into a diffraction grating to generate a spectrum of white light, and irradiates a subject by the spectral sequence. Only light corresponding to each wavelength of the spectral sequence reaches each position on the subject, so measuring the reflectance of the spectral sequence yields one-dimensional reflectance information. Moving the reflectance information along the direction of another axis yields a two-dimensional image. That is to say, the wavelength information is converted into position information, and an image is obtained from the reflectance for each position information. However, the technique described in U.S. Pat. No. 6,341,036 yields a monochrome image, and a color image cannot be obtained.

A technique is proposed in U.S. Pat. No. 9,254,089 to colorize an image in SEE. U.S. Pat. No. 9,254,089 describes a technique to generate white illumination light by guiding light of different wavelengths from each other by three different fibers and inputting to the same diffraction grating at different angles, to obtain a color image.

However, when the technique of U.S. Pat. No. 9,254,089 is used, three mechanisms that rotatively connect to the respective fibers become necessary, which makes the mechanisms complex. In addition, the three fibers are bundled together for use, which leads to shortcomings in that the fiber portion becomes thick.

When forming a color image, reflected light of this white illumination light is input, and spectroscopic measurement is performed using a spectroscope, to calculate the reflectance for each wavelength. In other words, in forming an image, a spectroscopic measurement is performed using a spectroscope to capture the reflected light of the white illumination light and to calculate the reflectance of each wavelength. In the case of a spectroscope that has one diffraction grating and one imaging system, wavelength bands on an imaging device corresponding to the red, green, and blue colors, have a particular distribution of the red, green, and blue colors such that the resolution of the image is primarily dependent on the resolution of the green wavelength band. The wavelength that is between the red and green and that is considered to be unused is, specifically, orange. Since human eyes are most sensitive to green, the resolution of the image is almost determined by the green wavelength band. Such an association with the green wavelength band is due to sensitivity of the human eye, so increasing the resolution of green increases the resolution of the ultimate image. While raising the resolution of green raises a final image resolution, the resolution of green, however, on the detector of the spectrometer is low or decreases, and, therefore, improving the resolution is difficult. For example, since the unused wavelength region exists, the resolution of green on an image pickup element of a spectroscope decreases with the unused wavelength region, making improvement of the resolution difficult.

SUMMARY OF THE INVENTION

Accordingly, it is a broad object of the present disclosure to provide SEE apparatuses, systems, methods, and storage mediums for use with same.

In at least one embodiment a two-dimensional image acquiring apparatus may include: a Spectrally Encoded Endoscopy ("SEE") probe including at least one diffractive element and one or more optical fibers, the at least one diffractive element operating to separate and diffract a transmitted light into a first plurality of light fluxes of different wavelength bands such that the diffracted light beams are overlapped or superposed or substantially overlapped or substantially superposed on a target region; a diffraction grating configured to receive a light and to disperse or emit the received light into or as a second plurality of light fluxes of different wavelength bands; at least one image sensor or detector that operates to acquire one or more intensities or spectral information from the received light; and at least one imaging optical system that operates to image the plurality of light fluxes dispersed or emitted from the received light, wherein the at least one diffractive element, the at least one imaging optical system, and the at least one image sensor or detector are disposed for each of the plurality of light fluxes dispersed or emitted from the received light to acquire spectral data of each of the plurality of light fluxes, and wherein the at least one diffractive element operates to rotate such that an image of the at least one image sensor or detector is changed, and a two-dimensional image is acquired from the image.

In another embodiment, a spectroscope or spectrometer may include: a collimator that operates to receive a light flux from a light source; a diffraction grating; and an imaging device, wherein the number of light fluxes entering the collimator is plural, and positions of a plurality of spectral sequences imaged at positions on the imaging device are relatively shifted in a direction parallel to a direction in which wavelengths of the spectral sequences are arrayed.

In at least one embodiment, a spectral apparatus may include: a collimator that operates to form a light flux from a light source into a parallel light flux; a light flux splitter configured to split the light flux emitted by the collimator into a plurality of light fluxes, the angle of travel of each light flux of the plurality of light fluxes being different; a diffraction grating configured to emit each of the plurality of light fluxes at a different angle according to wavelength; an imaging optical system configured to collect the light emitted from the diffraction grating; and at least one light sensor or detector disposed near a focal point of the imaging optical system, and configured to acquire spectral information of the reflected and scattered light, wherein the light flux splitter is configured so that the plurality of light fluxes are overlaid at an incident pupil of the imaging optical system.

In one or more embodiments, a method for controlling a two-dimensional image acquiring apparatus may include: defining a spectrum of wavelength ranges to use for acquiring the two-dimensional image such that the spectrum bands overlap or substantially overlap at a target region; receiving light reflected from the target region; separating the received light into two or more light fluxes having different wavelengths; and imaging the light fluxes separated from the received light to acquire or generate the two-dimensional image.

In one or more embodiments, a computer-readable storage medium storing at least one program that operates to cause one or more processors to execute a method for controlling a two-dimensional image acquiring apparatus, where the method may include: defining a spectrum of wavelength ranges to use for acquiring the two-dimensional image such that the spectrum bands overlap or substantially overlap at a target region; receiving light reflected from the target region; separating the received light into two or more light fluxes having different wavelengths; and imaging the light fluxes separated from the received light to acquire or generate the two-dimensional image.

In at least one embodiment, an image acquisition apparatus may include: a light source; an optical branching part configured to branch light from the light source into a plurality; one collimator configured to form the plurality of light fluxes emitted from the optical branching part into a plurality of parallel beams; one spectral part configured to disperse the multiple parallel beams; one imaging optical system configured to image the dispersed light fluxes as a plurality of different images; and at least one imaging device disposed near the focal point of the imaging optical system, wherein the spectral part is disposed above the iris of the imaging optical system, and wherein pixels on the imaging device that correspond to the same wavelength in the plurality of different images are shifted as to each other in the direction in which wavelengths are arrayed.

In color imaging for a SEE device, deterioration in resolution of green regions that determine resolution when images are formed is countered by obtaining data from pixels shifted as to each other with respect to wavelength, which may enable the effects of pixel shifting to be obtained, so resolution can be improved.

In one or more embodiments, in order to perform imaging with such spectrally encoded endoscopy (SEE) at high sensitivity, there may be a need to use a multi-mode fiber with a large core diameter to raise light usage efficiency. Particularly, in a case where the tip portion of the endoscope probe moves away from the subject to measure a broad area of the subject, a multi-mode fiber with an even larger core diameter may be used to compensate for loss in sensitivity.

In SEE, position information of the subject is obtained by diffusing light transmitted over a multi-mode fiber, using a spectroscope. That is to say, in order to raise positional resolution for observing the subject in one or more embodiments, the wavelength resolution of the spectroscope has to be raised. In order to raise the wavelength resolution of the spectroscope without losing light usage efficiency in one or more embodiments, a large imaging optical system that has a large numerical aperture may be used, in order to reduce the core-diameter image imaged on the sensor of the spectroscope. An imaging optical system that has a large numerical aperture uses a large-sized lens and mirror, necessitating high manufacturing costs.

In accordance with at least one aspect of the present disclosure, an image acquisition apparatus that forms images with high light usage efficiency, at a low cost, is provided herein.

In at least one embodiment, an image acquisition apparatus according to at least one aspect of the present disclosure may include: a light source; a diffractive element configured to be irradiated by light emitted from the light source, and to split the light into light fluxes of different wavelength bands; a light irradiation unit by which a subject is irradiated by the light fluxes of different wavelength bands; an optical fiber configured to collect reflected and scattered light from the subject and perform fiber transmission thereof; a collimator configured to form a light flux emitted by the optical fiber into a parallel light flux; a light flux splitter configured to split the light flux emitted by the collimator into a plurality of light fluxes, the angle of travel of each being different; a diffraction grating configured to emit each of the plurality of light fluxes at a different angle according to wavelength; an imaging optical system configured to collect the light emitted from the diffraction grating; and a light receiving unit disposed near a focal point of the imaging light system, and configured to acquire spectral information of the reflected and scattered light. A two-dimensional image is acquired from a plurality of sets of spectral information acquired by the diffraction element being rotated to change a position of irradiated light on the subject. The light flux splitter is configured so that the plurality of light fluxes are overlaid at an incident pupil of the imaging optical system.

In at least a further embodiment, an image acquiring apparatus according to at least a further aspect of the present disclosure includes a light source, a diffraction grating that transmits light from a light source through a fiber, projects the light that has been transmitted to a diffraction element, diffracts and projects a diffracted luminous flux spectrally dispersed with the diffraction element so that diffraction light with different diffraction orders overlaps on a testee (or subject), transmits the light reflected and scattered by the testee (or subject) through a fiber, and separates once more, per wavelength, the light that has been transmitted, an imaging optical system that forms the luminous flux that has been spectrally dispersed into an image, an image pickup element that is disposed near a focal point of the imaging optical system, in which an image on the image pickup element is changed by rotation of the diffraction element to acquire a two-dimensional image from the image, and at least one wavelength band splitting element that splits the light that has been transmitted into a plurality of wavelength bands. In the image acquiring apparatus, luminous fluxes that have been split with the wavelength band splitting element are incident on the imaging optical system at different angles, and the luminous fluxes that have been spectrally dispersed per wavelength with the diffraction grating are formed on the image pickup element into an image that practically has no gap in a spectrally dispersed direction.

In colorization of a spectrally encoded endoscopy (SEE), using higher order diffraction light of a diffraction element provided at a distal end, white illumination light generated by overlapping various diffraction light of various diffraction orders in red, green, and blue areas is generated and is illuminated on a testee (or subject), a plurality of wavelength band splitting elements are provided in an optical path that guides light reflected by the testee to an image pickup element of a spectroscope, and while performing optimization, the wavelength bands are arranged on the image pickup element to form an image. With the above, the resolution of the acquired image can be improved without decreasing the utilization efficiency of the acquired light.

According to the present disclosure, an image acquisition apparatus that forms images with high light usage efficiency may be provided at a low cost.

In accordance with at least another aspect of the present disclosure, the SEE technique(s) discussed herein may be employed to reduce the cost of at least one of manufacture and maintenance of SEE devices, systems and storage mediums by reducing or minimizing a number of optical components in an interference optical system, such as an interferometer.

In accordance with at least a further aspect of the present disclosure, the SEE technique(s) discussed herein may be used in or used with an interference optical system, such as an interferometer.

According to other aspects of the present disclosure, one or more additional apparatuses, one or more systems, one or more methods, and one or more storage mediums using SEE technique(s) are discussed herein. Further features of the present disclosure will become apparent from the following description of exemplary embodiments with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIG. 2 is a diagram describing a colorizing technique in at least a SEE system.

FIG. 3 is a diagram describing a colorizing principle in at least a SEE system.

FIG. 6 is a diagram for describing a layout realizing pixel shifting in at least the first embodiment.

FIGS. 7A and 7B are diagrams illustrating a preferable layout of detection fibers.

FIG. 8 is a diagram illustrating the configuration of a spectroscope in at least a second embodiment.

FIG. 12 is a diagram illustrating an overview of fixed pattern correction processing of an image according to at least one embodiment of the present disclosure.

FIGS. 27A to 27C are diagrams illustrating an arrangement of spectral sequences on the image pickup element according to at least the seventh embodiment.

DETAILED DESCRIPTION OF THE EMBODIMENTS

One or more devices, optical systems, methods, and storage mediums for improving resolution of an image of a subject, such as tissue, using a SEE technique and/or for obtaining a black and white image and/or a color image using a SEE technique are disclosed herein. In accordance with at least one aspect of the present disclosure, one or more devices, optical systems, methods, and storage mediums discussed herein use a SEE technique to improve image resolution and/or to obtain images in black and white and/or color while improving the resolution.

At least a first embodiment of the present disclosure is described herein (with a further or alternative embodiment being shown in FIG. 1B and an even further or other alternative embodiment being shown in FIG. 1C as discussed below) with reference to FIGS. 1A to 6. A pixel-shift configuration using two imaging devices will be described in at least the first embodiment. Description will be made according to the technique disclosed in U.S. Pat. No. 9,254,089 that uses three fibers for the colorization technique. Note, however, that techniques regarding colorization, and the embodiments of the present disclosure, are not restricted to this.

Figure 1A:
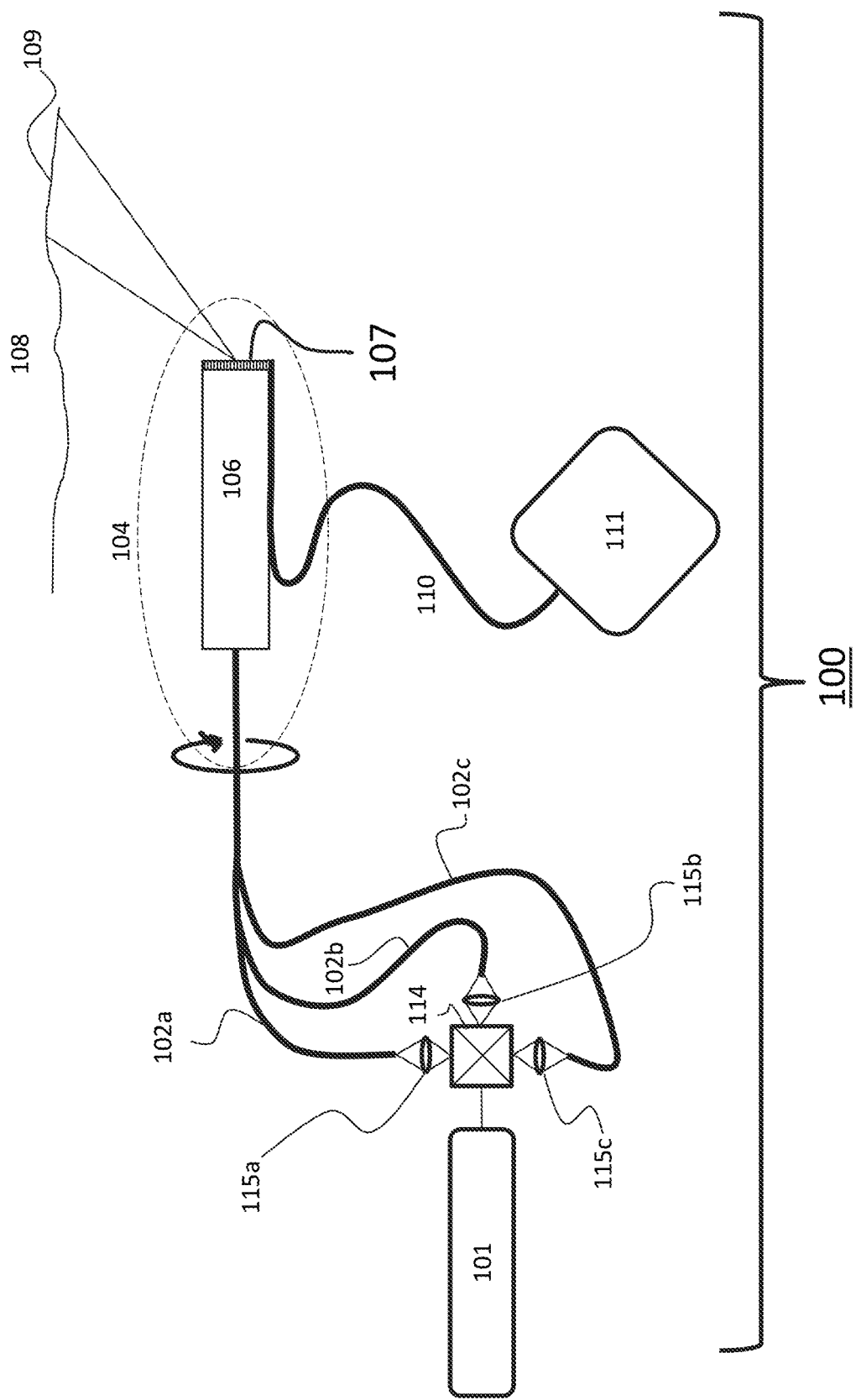
FIG. 1A is a SEE system diagram according to at least a first embodiment in accordance with one or more aspects of the present disclosure.
Figure 1B:
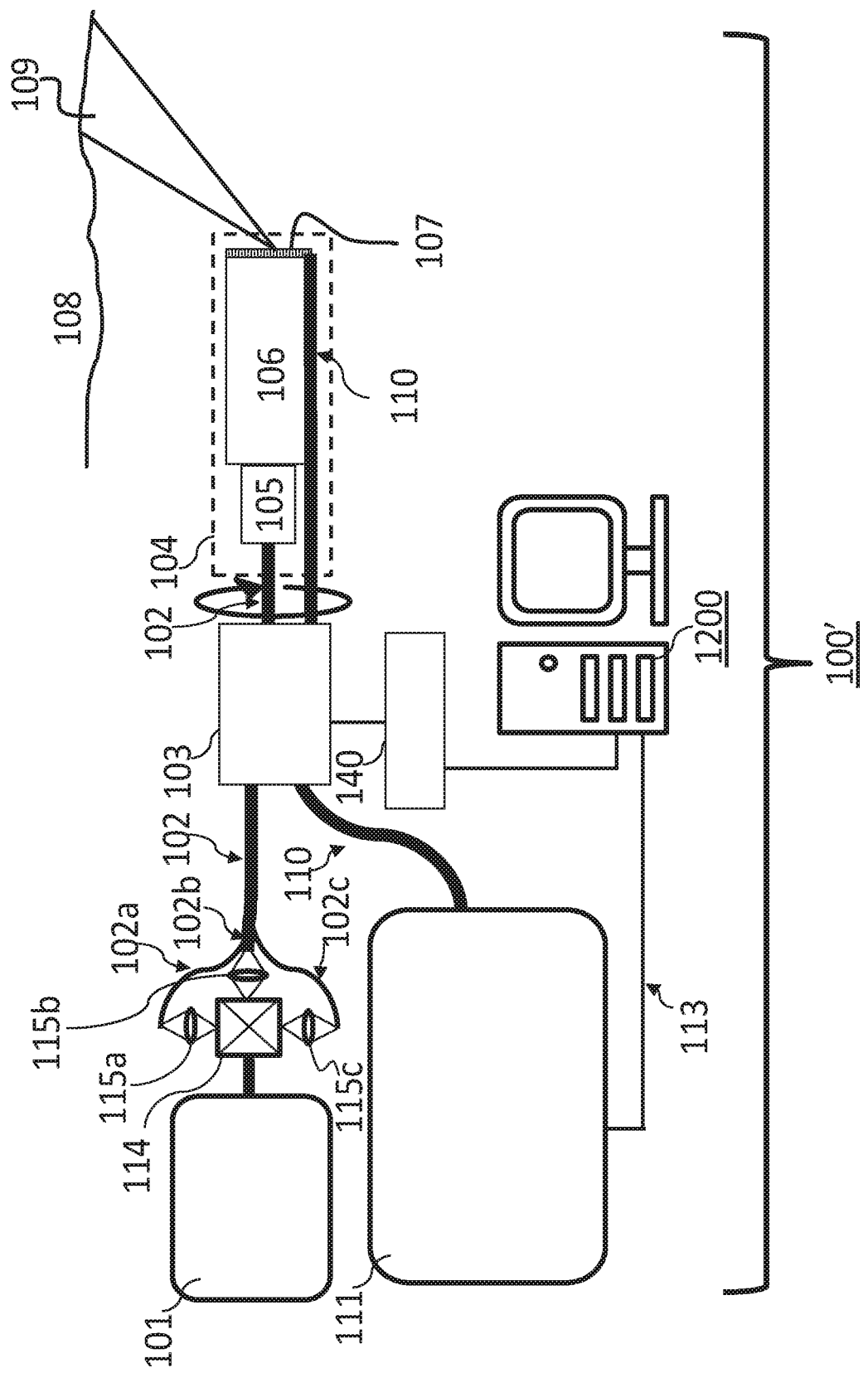
FIG. 1B is a system diagram of a SEE system according to at least a further embodiment in accordance with one or more aspects of the present disclosure.
Figure 1C:
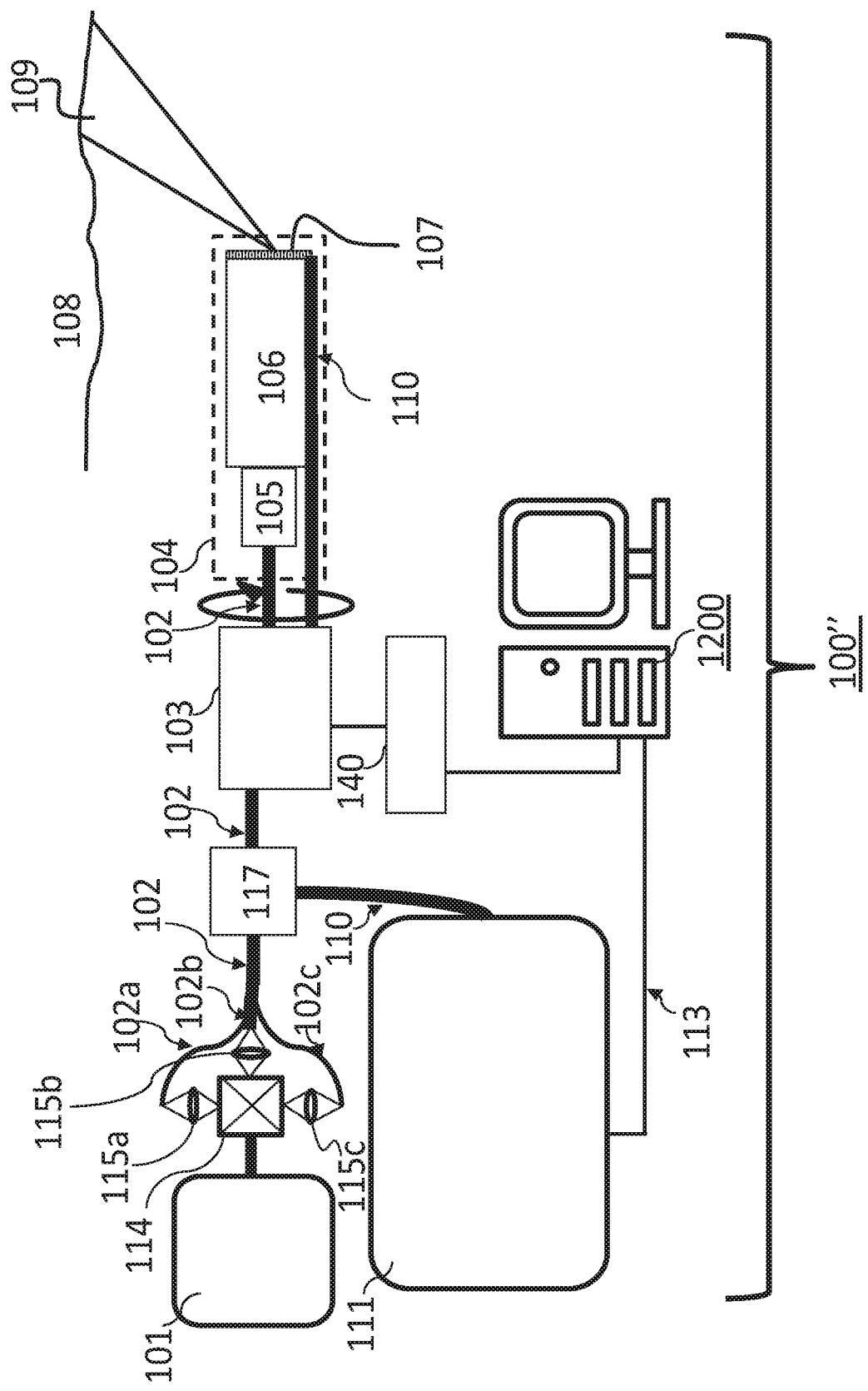
FIG. 1C is a system diagram of a SEE system according to at least a further embodiment in accordance with one or more aspects of the present disclosure.

As shown in at least FIG. 1A, white light from a white light source 101 is input to a dichroic mirror 114, split into RGB colors, and input by coupling optical systems 115a through 115c into transmission fibers 102a through 102c, and transmitted. The light fluxes of the RGB colors that have been transmitted enter a tip diffraction grating 107 provided on the tip of a probe unit 104 (which in one or more embodiments may include at least one of: a spacer 106, a GRIN lens 105, the diffraction grating 107, etc. as shown in one or more of FIGS. 1A-1C). The light fluxes diffracted by the tip diffraction grating 107 are diffracted according to different diffraction angles for each wavelength thereof, forming irradiation spectral sequences 109a through 109c on a subject 108 (for example, in at least one embodiment, 109a is the sequence from $R_{\lambda,1}$ to $R_{\lambda,2}$, 109b is the sequence from $G_{\lambda,1}$ to $G_{\lambda,2}$, and 109c is the sequence from $B_{\lambda,1}$ to $B_{\lambda,2}$ as shown in FIG. 3). The incident angle to the tip diffraction grating 107 is changed for input of each RGB color, as described in U.S. Pat. No. 9,254,089. FIG. 1C illustrates an alternative embodiment of a SEE system 100" including a spectrometer as shown in FIG. 1B (see e.g., system 100'), with the exception being that a deflecting or deflected section 117 is incorporated into the system 100' of FIG. 1B such that the cable or fiber 102 connecting the light source 101 to the rotary junction 103 and/or the probe section 104 and the cable or fiber 110 connecting the spectrometer 111 to the rotary junction 103 and/or the probe section 104 pass through, and are connected via, the deflected section 117 (discussed further below). Specifically, the transmission fibers 102a through 102c are laid out at different positions in a single line as illustrated in FIG. 2, so that the output light fluxes match on the tip diffraction grating 107. By distancing the transmission fibers 102a through 102C for the RGB colors by an appropriate distance, the irradiation spectral sequences 109a through 109c formed for each color can be made to be overlaid on the subject 108. Each of the irradiation spectral sequences 109a through 109c formed on the subject 108 being overlaid forms quasi-white light (see e.g., FIG. 3). Additionally or alternatively, the light emitted by the white light source 101 may be transmitted by the illumination light transmission fiber 102 and is incident on the probe portion 104 via a deflecting or deflected section 117 and via a rotary junction (hereinafter, RJ) RJ 103 (e.g., the fiber 102 may extend through the RJ 103 and into the probe portion 104) (as best seen in FIG. 1C) or via the RJ 103 without the deflecting or deflected section 117 (best seen in FIG. 1B).

In at least one embodiment, the console or computer 1200, 1200' operates to control motions of the RJ 103 via a Motion Control Unit (MCU) 140, acquires intensity data from the detector(s) in the spectrometer 111, and displays the scanned image (e.g., on a monitor or screen such as a display, screen or monitor 1209 as shown in the console 1200 of FIG. 34 and/or the console 1200' of FIG. 35 as further discussed below). In one or more embodiments, the MCU 140 operates to change a speed of a motor of the RJ 103 and/or of the RJ 103. The motor may be a stepping or a DC servo motor to control the speed and increase position accuracy.

Figure 4A:
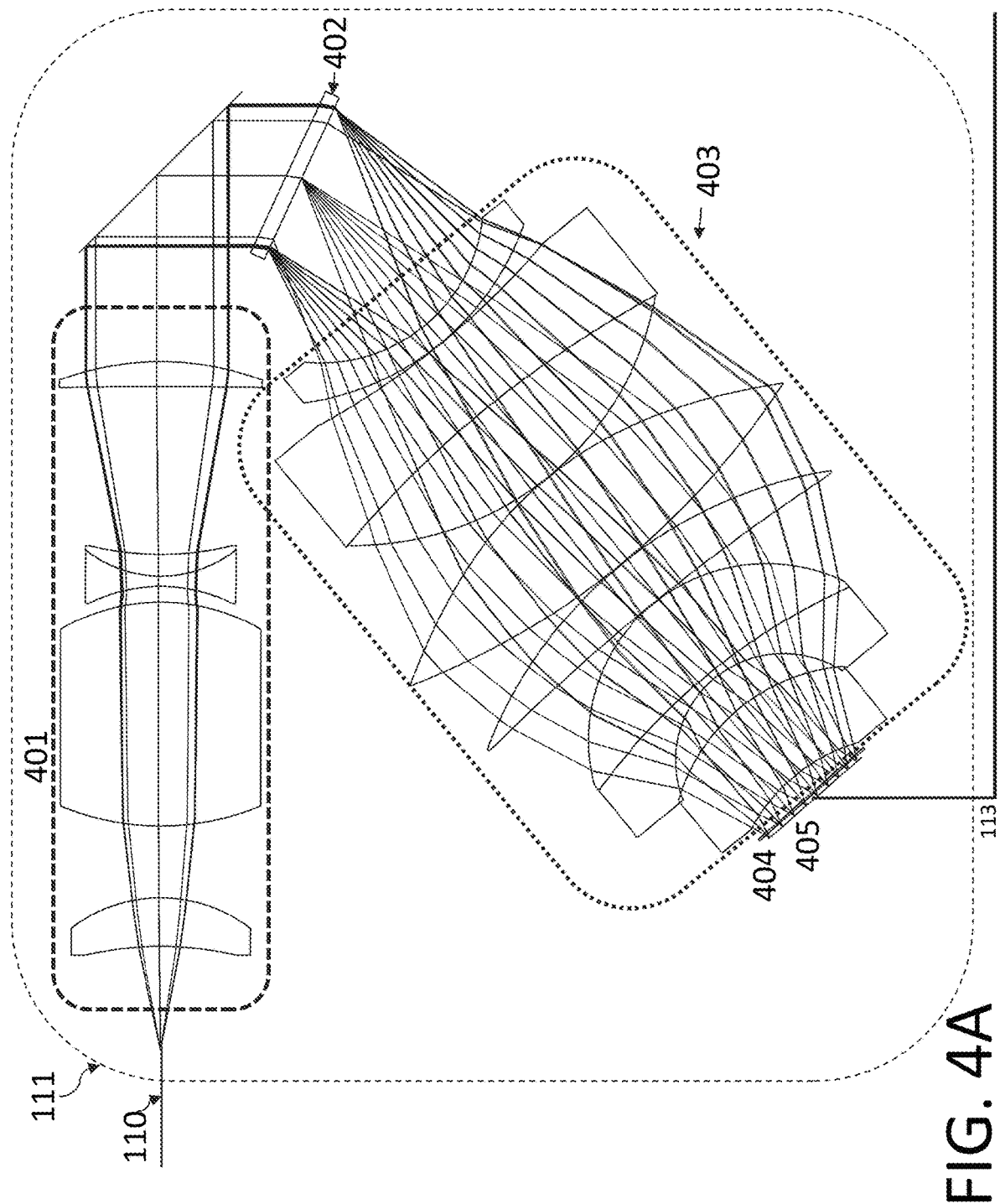
FIGS. 4A and 4B are diagrams illustrating the configuration of a spectroscope according to at least the first embodiment.

Reflected light of this quasi-white light is transmitted by a detection fiber 110, and is input to a spectroscope 111. The spectroscope 111 has a collimator lens 401, a diffraction grating 402, an imaging lens 403, and a one-dimensional imaging device 404, as illustrated in FIG. 4A. Light emitted from the detection fiber 109 is changed into a parallel light flux by the collimator lens 401, and enters the diffraction grating 402. The light flux diffracted by the diffraction grating 402 is split into wavelengths, and enters the imaging lens 403. The light flux is formed into a signal spectral sequence 405 image on the one-dimensional imaging device 404 by the imaging lens 403.

Figure 5:
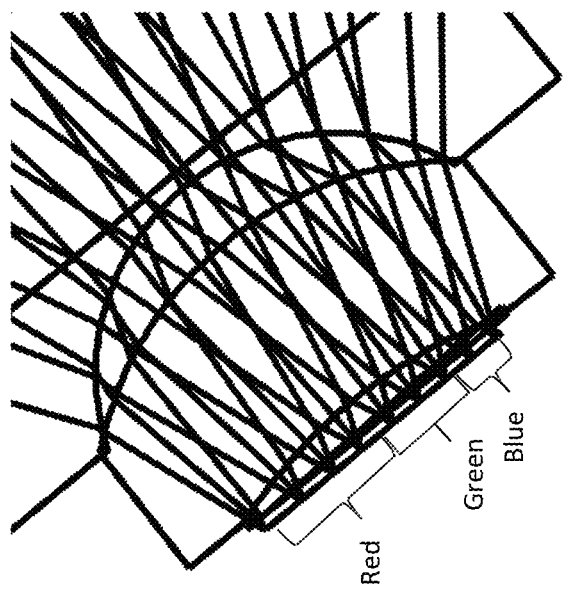
FIG. 5 is a diagram illustrating distribution of colors on an imaging device within a spectroscope according to at least the first embodiment.

Considering a signal spectral sequence formed on a one-dimensional imaging device, in a case of forming light of each wavelength band of R, G, and B on one one-dimensional imaging device, the regions of each will be imaged in a certain range, as illustrated in FIG. 5. As long as the same diffraction grating is being used at this time, the ranges of the RGB regions on the one-dimensional imaging device are unavoidably such that B is imaged at a narrowest range, and R at a broadest range, due to the relationship between wavelength and diffraction angle. The region of G that has the highest greatest relative luminosity is most influential on the resolution of the color image, so the higher the resolution of G is, the higher the resolution of obtained images can be made to be. However, it is difficult to raise the resolution of G beyond a certain level due to the relationship between wavelength and diffraction angle, as described above. Accordingly, as a method to raise the resolution of G, two one-dimensional imaging devices are prepared, and the pixels on the one-dimensional imaging devices are shifted from each other, to improve resolution.

Figure 4B:
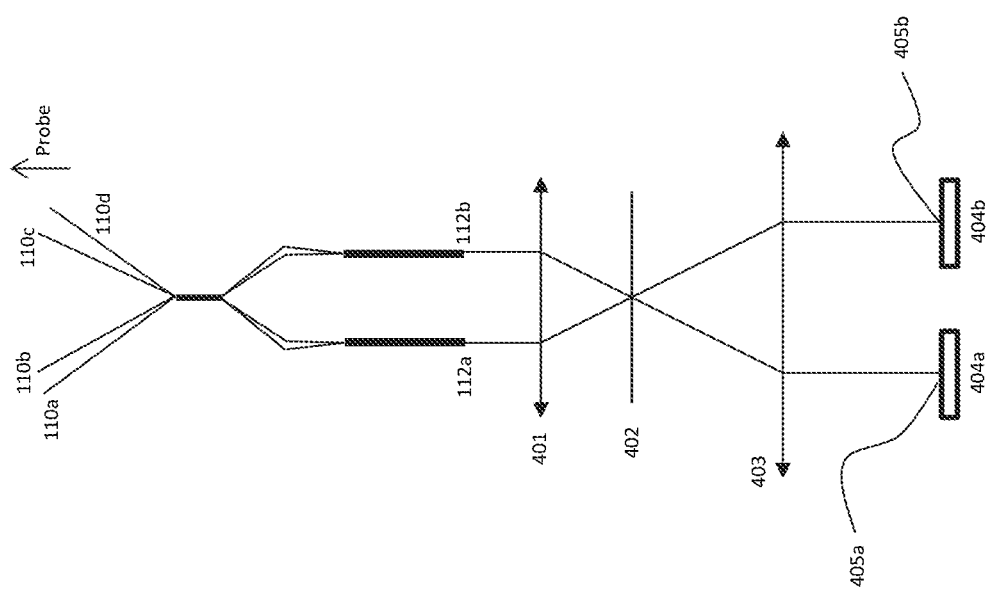

Multiple detection fibers 110 are prepared (the four of 110a through 110d there) as illustrated in FIG. 4B. The detection fibers are bundled two each, and light is input to the collimator lens 401. The detection fibers 110a through 110d are divided into two sets, so there are two emission ends (112a and 112b). Disposing the two emission ends away from each other yields two emission light fluxes, which are input to the diffraction grating 402. The light fluxes diffracted by the diffraction grating 402 are input to the imaging lens 403, and form two signal spectral sequences 405a and 405b. The signal spectral sequences 405a and 405b are detected by two one-dimensional imaging devices 404a and 404b in at least one embodiment. In one or more embodiments, the signal spectral sequences 405a and 405b are preferably sufficiently distanced from each other when being formed, taking into consideration that the two one-dimensional imaging devices 404a, 404b will have packages and the like. Accordingly, the two emission ends formed by the detection fibers 110a through 110d also need to be disposed with sufficient distance therebetween.

In at least one embodiment, the two one-dimensional imaging devices 404a and 404b are situated with positions shifted by the equivalent of exactly ½ pixel, as illustrated in FIG. 6. This layout allows the two one-dimensional imaging devices 404a and 404b to capture slightly different signal spectral sequences. Thus, processing signals from the two one-dimensional imaging devices 404a, 404b enables signal spectral sequences of higher resolution to be acquired. Processing equivalent to that of an imaging apparatus in Japanese Patent Laid-Open No. 9-172568 and so forth may be used in the pixel-shift imaging in one or more embodiments, so details thereof will not be described here.

Using such a configuration improves the resolution of the G region which is a narrow range on the imaging device, and consequently, the resolution of the obtained image can be improved. Although the resolution is not doubled by this method, resolution improvement in the order of tens of percent may be achieved.

The number of detection fibers is set to four, and the number of branches to two, in the present embodiment, but this is not restrictive. For example, an arrangement may be made where the number of detection fibers is 20, bundled five each for a total of four light fluxes being emitted, and four one-dimensional imaging devices each being laid out shifted by ¼ pixels. Thus, there is no restriction on the number of detection fibers and the number of branches thereof. However, the number of detection fibers included in each bundle of branched fibers preferably is the same for all bundles. If the number is different, there is a possibility that there may be a great difference in the brightness of signal spectral sequences at different imaging devices, which would affect subsequent image processing. Accordingly, the number of detection fibers preferably is an integer multiple of the number of branches. Furthermore, the integer is preferably 2 or greater. That said, in one or more embodiments, the number of detection fibers included in each bundle of branched fibers may be different for one or more bundles.

In at least one embodiment, the detection fibers are laid out cylindrically as illustrated in FIG. 7A. The layout of fibers in a case where the number of branches is N will be described here. The number of fibers on, for example, a cylinder is an integer multiple of N, so FIGS. 7A and 7B illustrate an example where N=3 and the number of detection fibers is 12. When the end or edge faces are numbered 1, 2, and 3, the reverse-side end or edge faces of the detection fibers (the incident side of detection light) preferably are laid out in the order of 1, 2, and 3, from the fiber connected to end or edge face 1, and finally returning to 1. Thus, the difference in detection efficiency according to the positions on the cylinder are averaged out in this embodiment configuration, and the brightness of the signal spectral sequences can be matched.

Although at least the first embodiment illustrates signal spectral sequences being imaged on the imaging devices by a single imaging lens, this is not restrictive. For example, a dichroic mirror may be inserted between the collimator lens (e.g., the collimator lens 401) and diffractive grating (e.g., the diffractive grating 402) or element to split into the respective wavelength bands, and have imaging lenses prepared for each split wavelength band. This enables the resolution to be improved for each wavelength band, and providing multiple imaging devices for each imaging lens can further improve resolution. Thus, branching into multiple light fluxes from detection fibers in a SEE spectroscope, forming multiple spectral sequences, and performing detection at multiple imaging devices used for detection by pixel shifting, enables the image resolution of the SEE to be improved.

At least a second embodiment of the present disclosure will be described with reference to FIG. 8. The second embodiment is an example where the photoreceptor used is not a one-dimensional imaging device but an area sensor (two-dimensional imaging device). Members which are denoted by the same reference numerals as in at least the first embodiment serve the same functions.

Figure 9A:
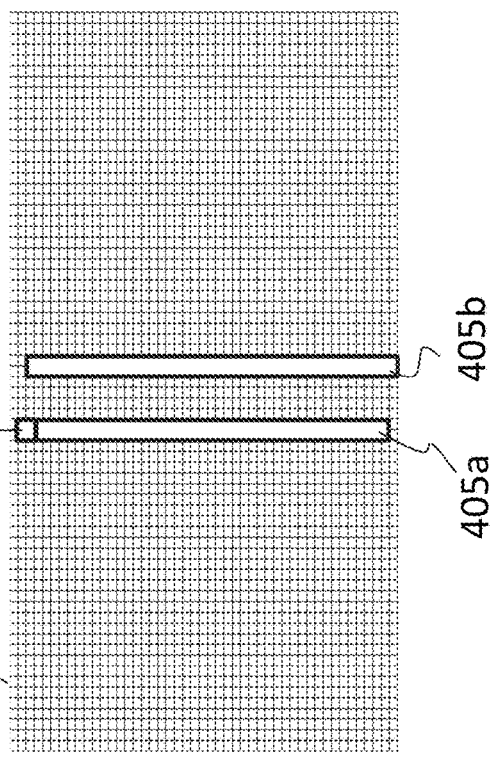
FIGS. 9A and 9B are diagrams for describing a layout realizing pixel shifting in at least the second embodiment.
Figure 9B:
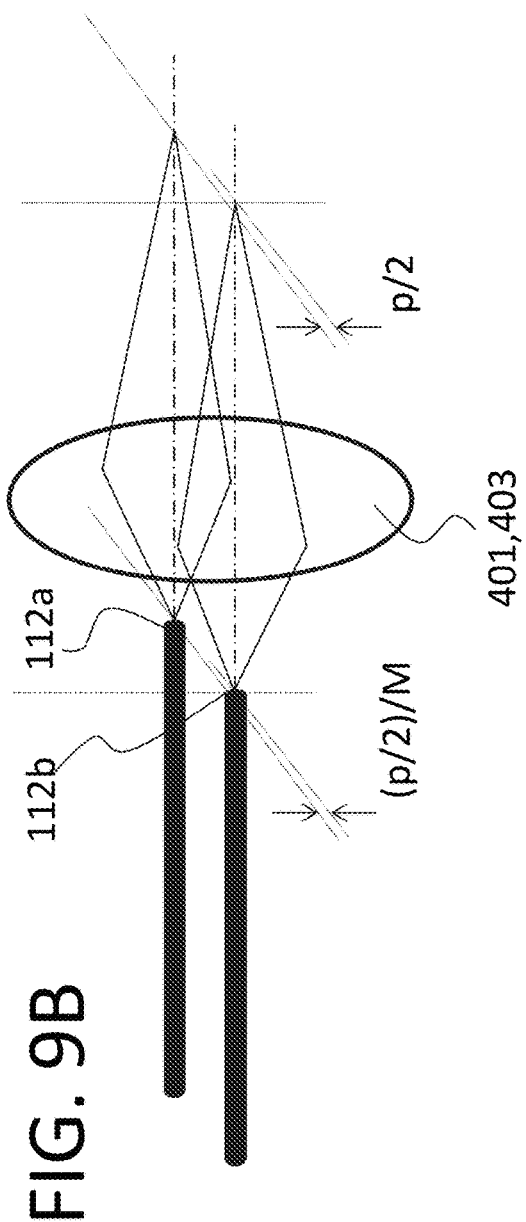

A single area sensor 801 is provided in at least the second embodiment, instead of the two one-dimensional imaging devices 404a, 404b in at least the first embodiment. Two signal spectral sequences 405a and 405b are formed on the area sensor 801, as illustrated in FIGS. 9A and 9B. Assumption will be made that the number of pixels of the area sensor 801 is sufficiently great or sufficient to operate as described herein. In at least one embodiment, a case where multiple pixels are read out at one time, rather than reading out all pixels one by one, will be considered, or may be used, for a readout of pixel information from the area sensor 801. For example, there conceivably are cases where sufficient readout resolution may be realized even by reading out multiple pixels at the same time, such as a case where the core diameter of fiber ends of the detection fibers 110 is great, and the optical image of the core diameter on the area sensor 801 is sufficiently larger than single pixels of the area sensor 801. This may further have advantages of achieving a faster readout and noise reduction. In the case of FIG. 9A, 2 by 2 pixels of the area sensor 801 are read out as a single signal.

Further, the emission ends 112a and 112b of the detection fibers are arrayed shifted from each other so as to be imaging on the area sensor 801 at a position shifted as to the direction at which the signal spectral sequences 405a and 405b are arrayed by one pixel. This configuration will be described with reference to FIG. 9B. FIG. 9B is a schematic diagram of the optical system of a spectroscope. Light fluxes emitted from the emission ends 112a and 112b pass through the collimator lens 401 and imaging lens 403, are enlarged or reduced by a magnification factor M, and are imaged on an area sensor that is omitted from illustration. The collimator lens 401 and imaging lens 403 are expressed here as a single lens, for the sake of simplicity (but, in one or more embodiments, as described herein, may be different lenses). In at least one embodiment, if the positions of the emission ends 112a and 112b are shifted in the vertical direction in FIG.

9B, shift equivalent to M times this shifting will also occur on the area sensor. Setting this shift amount to ½ times the readout size p on the area sensor enables shift of the signal spectral sequences 405a and 405b such as illustrated in FIG. 9A to be generated. Shifting by (p/2)/M as illustrated in FIG. 9B enables the signal spectral sequences 405a and 405b formed on the area sensor to be formed with shift of one pixel from each other. Since two pixels are taken as a single signal in readout, laying out the emission ends in this way results in the signal spectral sequences to be read out shifted by an amount equivalent to ½ pixels, so the pixels read out can have the advantages of pixel shifting.

Figure 10:
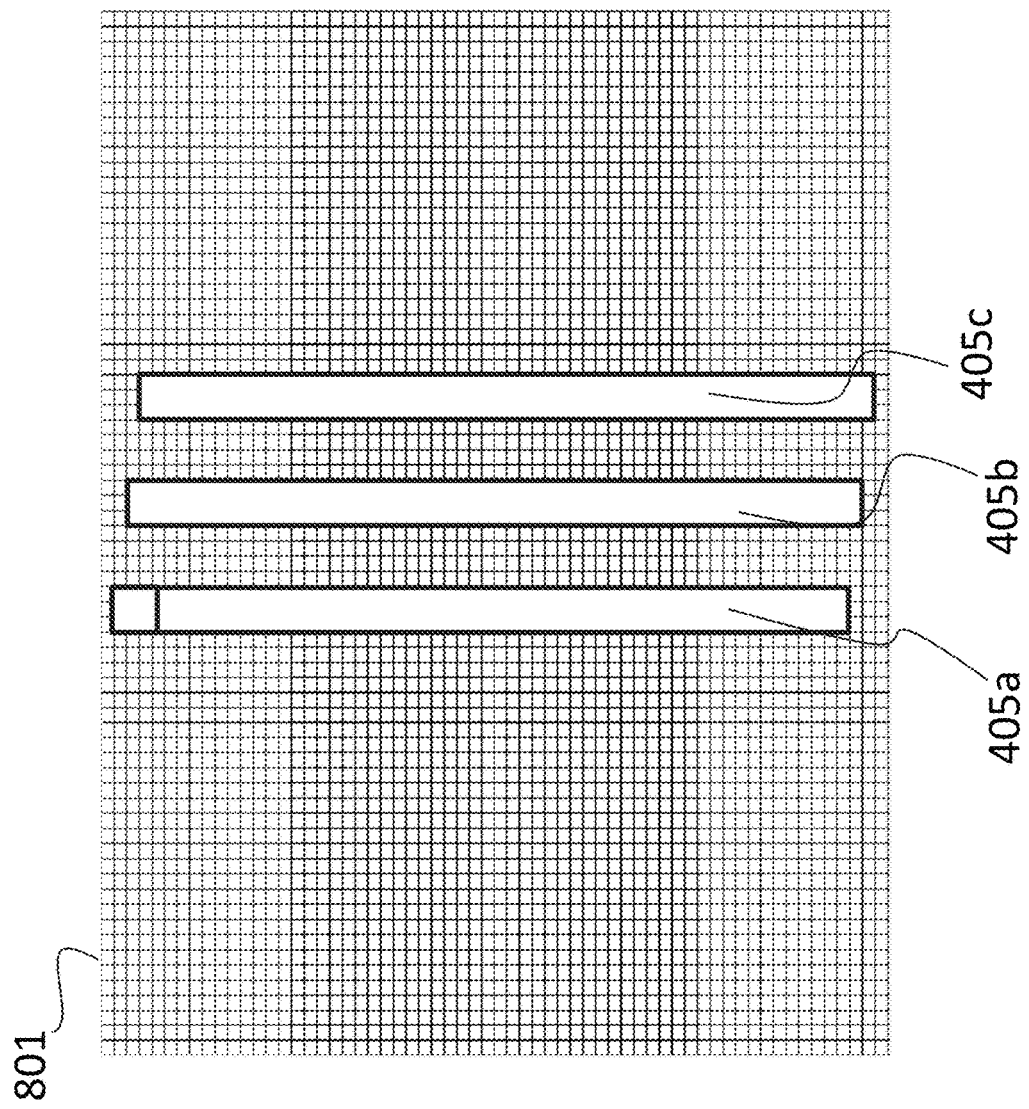
FIG. 10 is a diagram for describing a spectral sequence on an area sensor and another technique for readout.

Using this method enables three or more signal spectral sequences to be formed, if the size of the area sensor 801 orthogonal to the signal spectral sequences permits. An arrangement may be made where the readout of the area sensor 801 is 3 by 3 pixels, and three signal spectral sequences 405a through 405c that are shifted from each other by one pixel each may be achieved, to perform pixel shifting for the three (see e.g., FIG. 10). An arrangement where the number of detection fibers is six for example, with two each making up sets that are shifted by one pixel each, and forming signal spectral sequences on the area sensor 801, enables pixel shifting by three signals to be realized in at least one embodiment. In the same way, a suitable unit of pixel readout at a time for generating a single signal, and a suitable number for which pixel shifting is to be performed can be selected from the number of pixels of the area sensor, wavelength ranges of the signal spectral sequences, necessary resolution, and so forth, and readout of N pixels and N sets of pixel-shifting can be performed where N is an integer of 2 or larger.

In a case of using an area sensor, the signal spectral sequences can be separated by readout of the area sensor even if the signal spectral sequences are formed close to each other, so there may be no need to distance the emission ends 112a and 112b from each other like in at least the first embodiment, and the size of the collimator lens 401 can be reduced in at least one embodiment. It should be noted, however, that area sensors generally have lower readout speeds as compared to one-dimensional imaging devices, so the method according to at least the second embodiment may be somewhat disadvantageous with regard to realizing high speeds, while the method according to at least the first embodiment may more often lend itself to realizing high speeds.

Figure 11:
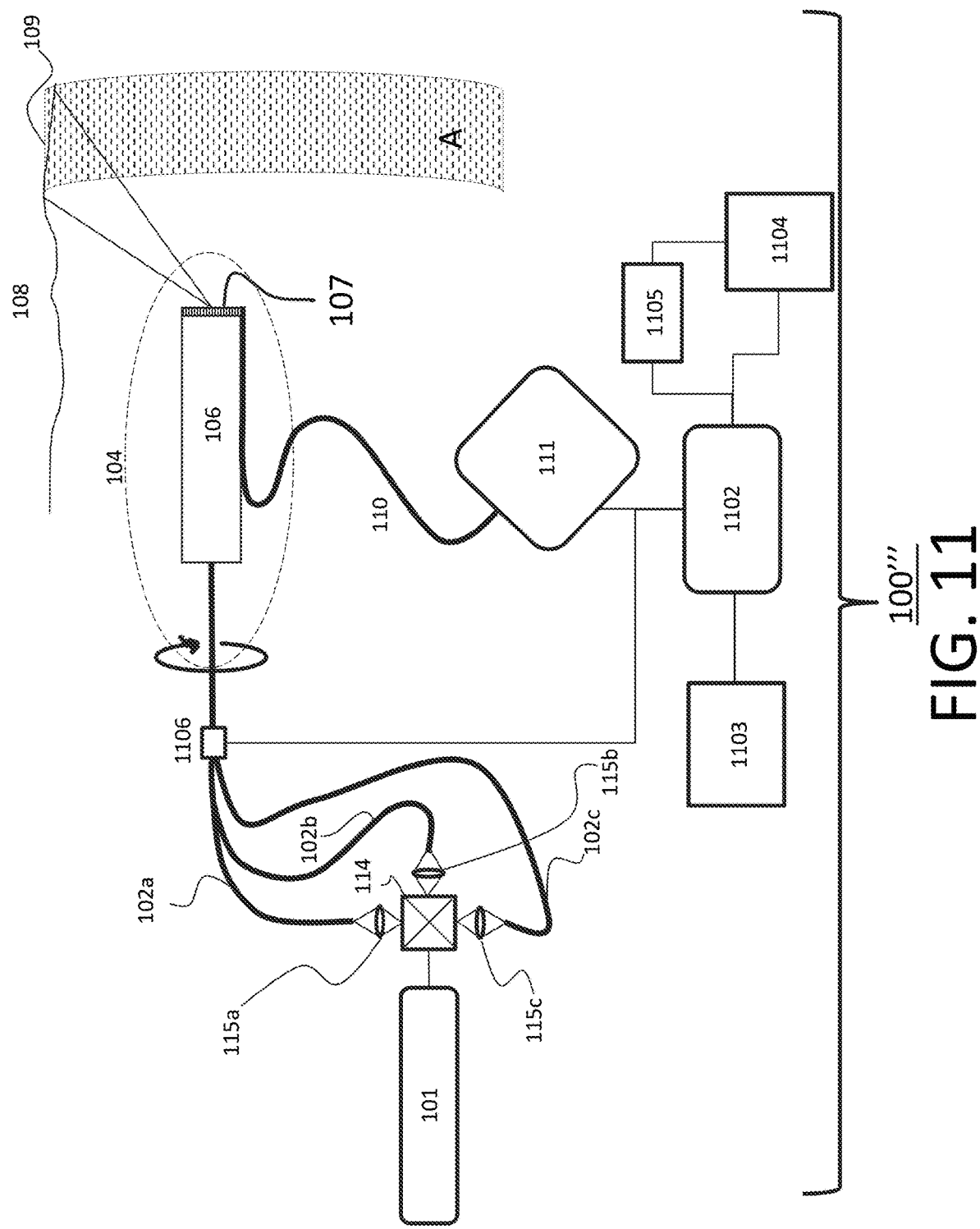
FIG. 11 is a diagram illustrating a configuration of an endoscope system in at least a third embodiment.

At least a third embodiment will be described with reference to FIG. 11. At least the third embodiment is a configuration example of an endoscope system using the optical system according to at least the first embodiment.

The spectrum information detected in the first embodiment is converted into signals at the spectroscope 111. At the time of this signal detection, the probe unit 104 is rotated centered on the longitudinal direction of the probe unit 104, using a motor 1106 (a motion control unit or MCU 140 may alternatively be used as discussed further below). Rotation of the probe unit 104 also rotates the formed irradiation spectral sequences 109, and a range of an area A in FIG. 11 is irradiated. The rotation and signal detection are synchronized, signal processing is performed as an image processing circuit 1102 (or, alternatively or additionally, using a processor or CPU such as a computer 1200 or 1200' discussed further below), and obtained image signals are arrayed, to form an image of the obtained data of the signal spectral sequences.

The signals that have been formed into an image are saved in a storage 1103 (or, alternatively or additionally, one of the other storage mediums discussed further below), and also displayed on a display 1104 (or, alternatively or additionally, one of the other displays discussed further below), and serve as material for diagnosis by a physician. A diagnosis support system 1105 or the like may be used to diagnose patients even more efficiently.

Figure 13:
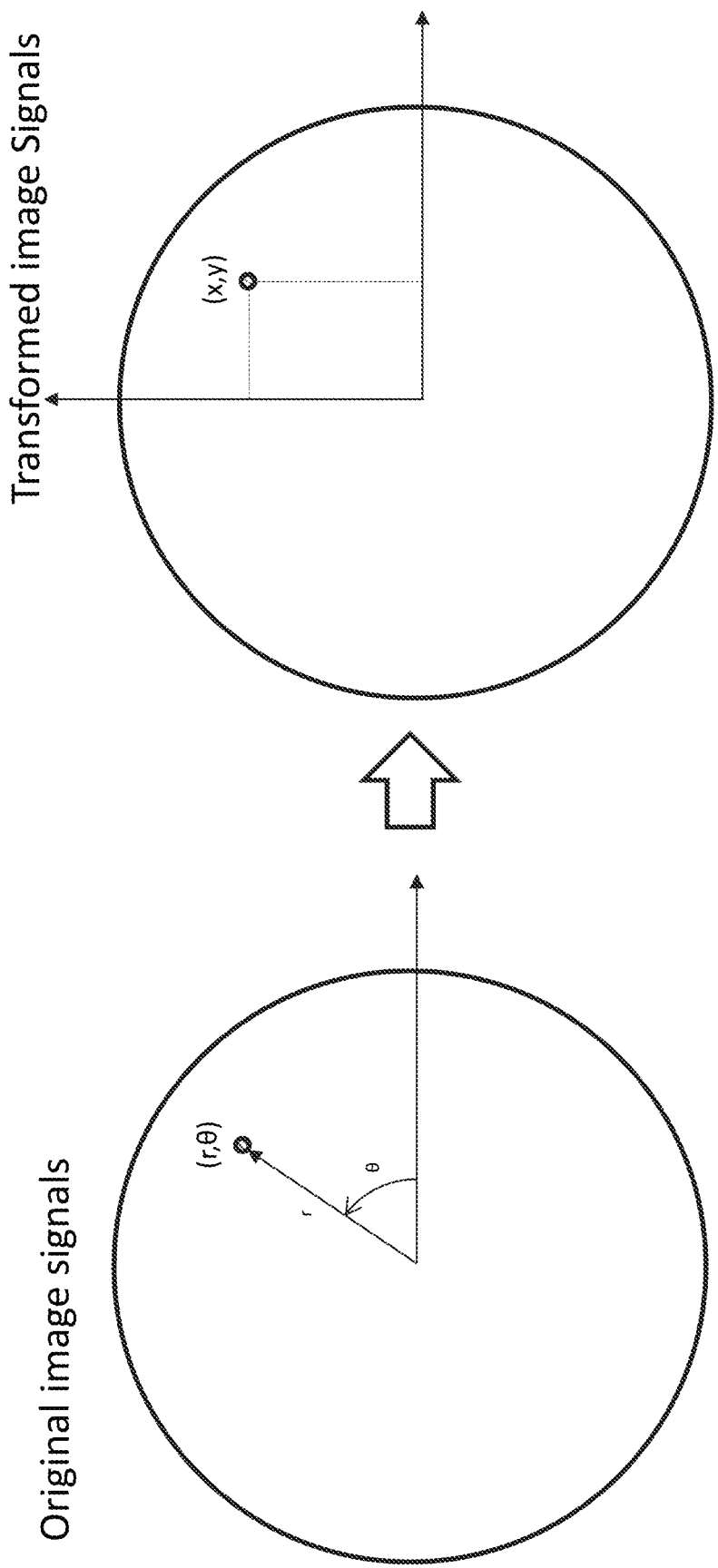
FIG. 13 is a diagram illustrating an overview of processing to convert an image from polar coordinates layout to X-Y two-dimensional layout, according to at least one embodiment of the present disclosure.

Image processing primarily involves rearranging of pixel signals to be formed into an image, brightness correction of the signals for each color of RGB, color balance and white balance correction that is necessary due to the wavelength of each RGB color being different from pixel to pixel, and so forth. If this correction is not performed, color change occurs as a fixed pattern when formed into an image. Accordingly, change in tone due to wavelength is corrected, so that an overall uniform tone is obtained (see e.g., FIG. 12). Because wavelength of light corresponding to each position in a radial direction is different, the intensity and/or color is different in each position in a radial direction (see left side of FIG. 12). As such, one or more embodiments may correct the color difference appearing in a fixed pattern to generate an image (see right side of FIG. 12). The signals of the obtained signal spectral sequences are of a circular image, and laid out according to polar coordinates, so rearranging the pixel signals is to rearrange into a two-dimensional x-y arrangement (see e.g., FIG. 13).

The resolution of the image primarily is dependent on the resolution of G, as described above. Accordingly, image processing is performed on the obtained image signals where the resolutions of R and B are raised or lowered so that the resolutions of R and B match the resolution of G.

This system configuration enables an endoscope according to SEE to be configured. It should be noted, however, that this system configuration is only exemplary, and that configurations of endoscopes according to SEE are not restricted to this system or to other systems described herein. Techniques for rearranging pixels, pixel number matching for RGB, and so forth, can be freely selected.

Figure 14:
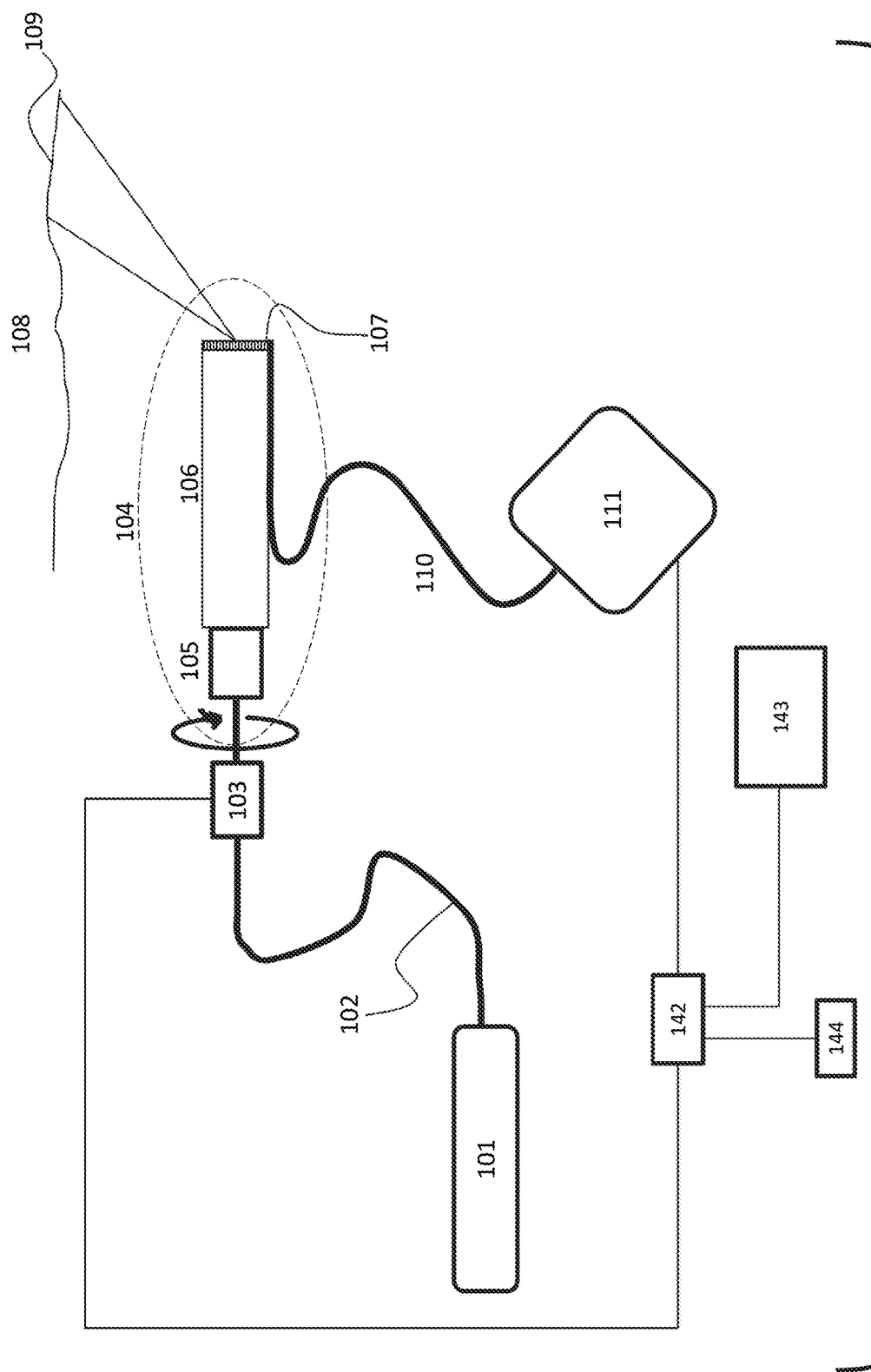
FIG. 14 is a schematic diagram describing a SEE system according to at least a fourth embodiment.

FIG. 14 illustrates a SEE system in its entirety, as an example of an image acquisition apparatus embodiment. Light emitted from a light source 101 is transmitted by an illumination optical fiber 102, and enters a light irradiation unit (also referred to herein as a probe unit) 104 via a rotary junction (hereinafter abbreviated to "RJ") 103. A white light source that includes light of frequency bands used for dispersion is used for the light source 101 in at least one embodiment. In the light irradiation unit 104, light that has been emitted from the core of the end portion of the illumination optical fiber 102 enters a spacer 106 via a refractive-index distribution lens (hereinafter referred to as "gradient index (GRIN) lens") 105. A diffraction grating (also referred to herein as a "diffraction element") 107 is formed at the tip portion of the spacer 106. A spectral sequence 109 is formed on a subject 108 by a light flux of white light entering the diffraction element 107.

Reflected light from the spectral sequence 109 is collected and transmitted at a detection optical fiber 110. Reflected light entering the core at the end portion of the detection optical fiber 110 within an angle range where light can be received is transmitted through the detection optical fiber 110, and input to a spectroscope 111. Although one detection optical fiber 110 is illustrated in FIG. 14, multiple detection optical fibers 110 may be provided surrounding the light irradiation or probe unit 104. Arraying multiple detection optical fibers 110 allows more light to be collected. One or more embodiments of using multiple fibers 110 are discussed herein.

Figure 15:
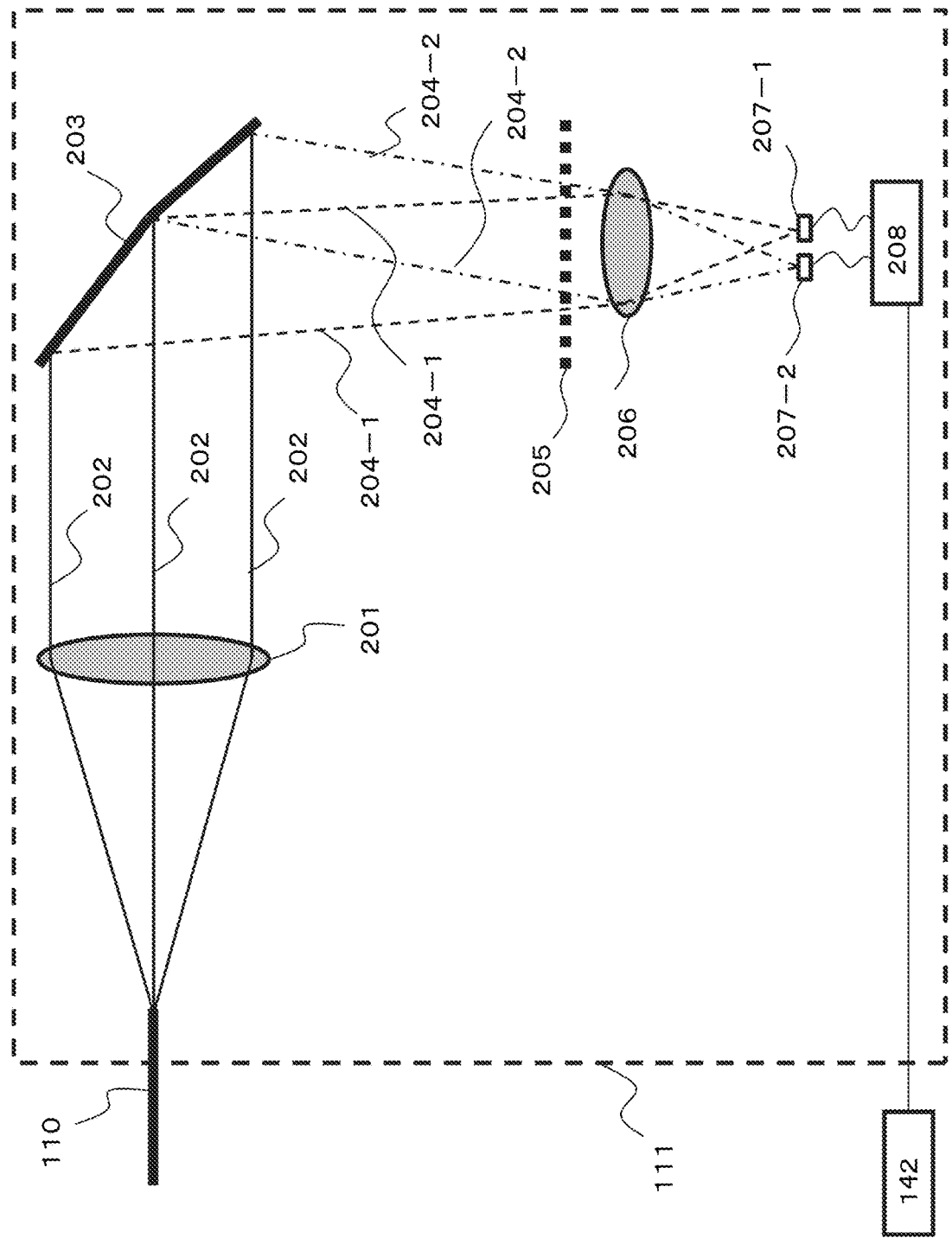
FIG. 15 is a schematic diagram describing a spectroscope according to at least the fourth embodiment.

FIG. 15 is a schematic diagram of at least one embodiment of the spectroscope 111. The spectroscope 111 acquires spectral information (relationship between wavelength and light intensity) of the input light. A light flux emitted from the core of the end portion of the detection optical fiber 110 is converted into a parallel light flux 202 by a collimator 201. The parallel light flux 202 is split into parallel light fluxes 204-1, 204-2, 204-3 (omitted from illustration in FIG. 15), and 204-4 (omitted from illustration in FIG. 15) by a light flux splitter 203.

Figure 16:
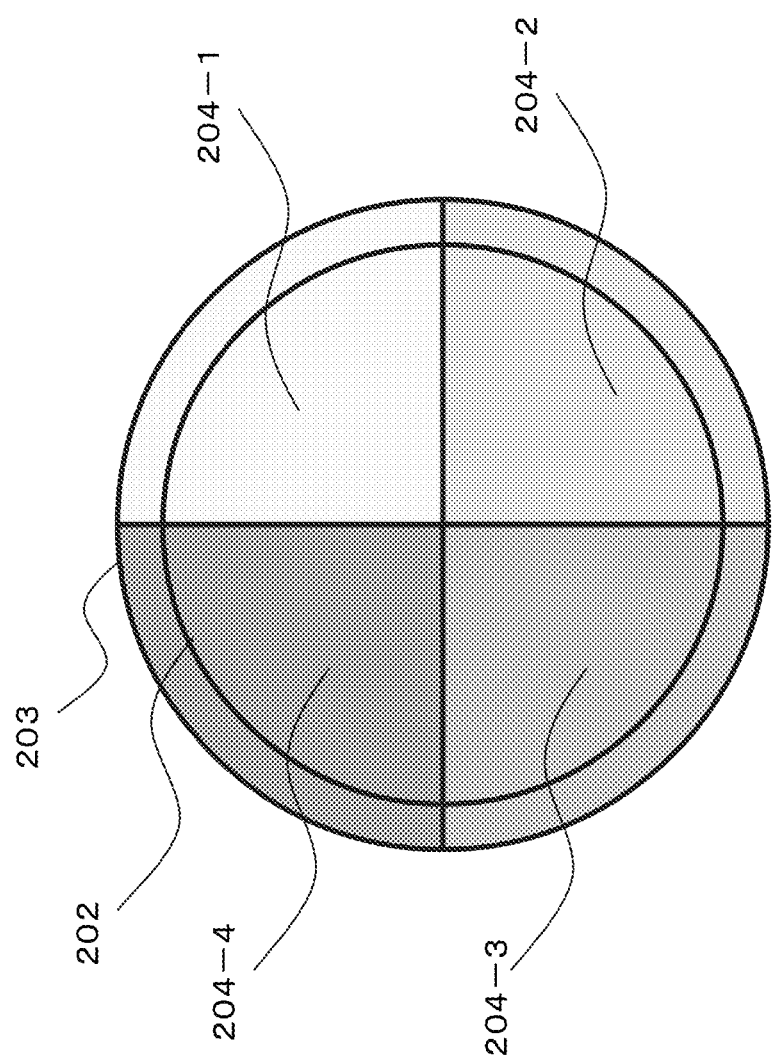
FIG. 16 is a schematic diagram describing a light flux splitting unit according to at least the fourth embodiment.

FIG. 16 is a schematic diagram of at least one embodiment of the light flux splitter 203, as viewed from the incidence direction of the parallel light flux 202. The light flux splitter 203 is made up of four mirrors of which the normal line directions are different. Reflecting the parallel light flux 202 at the light flux splitter 203 generates the parallel light fluxes 204-1 through 204-4. Tightly arraying the four mirrors so as to surround the parallel light flux 202 enables splitting into four light fluxes without losing light quantity of the parallel light flux 202. The four mirrors may be arrayed staggered in the depth direction in FIG. 16, i.e., in the direction in which the parallel light flux 202 travels.

The split light fluxes each travel in a different direction, and after having passed through a diffraction grating 205, enter an imaging optical system 206 overlaid on each other. Specifically, the light flux splitter 203 is configured such that the split light fluxes greatly overlap at an incident iris position of the imaging optical system 206.

Reducing the size of the light flux by half using the light flux splitter 203 enables the size of the mirror and lens making up the imaging optical system to be reduced. As a result, the spectroscope is reduced not only contributing to reduced space for the SEE system, but also enabling the cost of manufacturing the imaging optical system, which is a high-cost factor, to be reduced.

The light fluxes diffracted by the diffraction grating 205 are each imaged by the imaging optical system 206. Line sensors 207-1, 207-2, 207-3 (omitted from illustration in FIG. 15), and 207-4 (omitted from illustration in FIG. 15) are disposed at the focal position of the imaging optical system 206, and each of the parallel light fluxes 204-1, 204-2, 204-3, and 204-4 are collected and input. The line sensors are one-dimensional arrays of photoreceptors. Charge-coupled device (CCD) linear image sensors, complementary metal-oxide semiconductor (CMOS) linear image sensors, and so forth, can be used.

Figure 17:
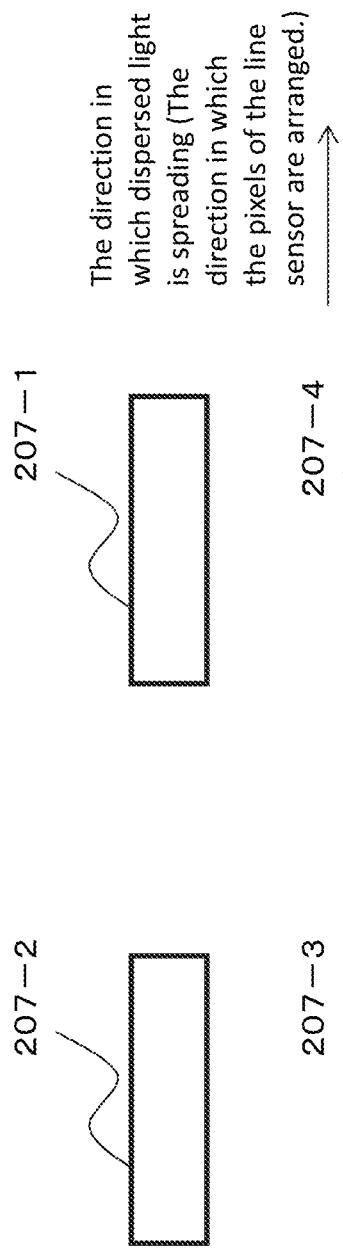
FIG. 17 is a schematic diagram describing a layout of line sensors according to at least the fourth embodiment.

FIG. 17 illustrates the layout of line sensors at the focal position of the imaging optical system 206. The line sensors that receive the two parallel light fluxes 204-1 and 204-2 are separated by a distance of $f \cdot \Delta\theta$, where $\Delta\theta$ radian is the difference in angle between the directions of travel of the two parallel light fluxes, and f is the focal distance of the imaging optical system 206. Assuming that the circumferential direction of the diffraction grating 205 is the parallel direction in the plane of FIG. 15, the spectral direction is the direction in which the line sensors 207-1 and 207-2 are arrayed, with the array of the pixels of the line sensors being laid out following the same direction.

In a case of using multiple detection optical fibers 110, the detection optical fibers 110 are arrayed in a direction perpendicular to the plane of FIG. 15. The cores of the end portions of the detection optical fibers 110 perform imaging on the line sensors 207-1 through 207-4, so erring in the layout direction will result in loss of wavelength resolution (i.e., positional resolution for forming an image of the subject). By arraying the fibers as described above, the array of imaging cores is perpendicular to the spectral direction (array of pixels), so wavelength resolution is not lost.

The line sensors 207-1 through 207-4 each convert the intensity of incident light into electric signals, and intensity information is obtained for each wavelength. The relationship between pixels of one-dimensional imaging devices and wavelengths preferably is calculated beforehand, using a light source of which the wavelength is known, such as a laser or the like, instead of the light source 101.

Light intensity information for each wavelength which the four line sensors have obtained is input to a computing unit 208 in at least one embodiment. The computing unit 208 calculates one set of spectral information (relationship between wavelength and reflected and scattered light intensity) by adding the output (electric signals) of pixels of the four line sensors where the wavelength is the same. The computing unit 208 is configured to an electrical circuit, calculator, etc. In one or more embodiments the computing unit 208 may be a part of or included in a computing system, such as, for example, a computer 1200, a computer 1200', etc., as discussed further below.

Figure 18:
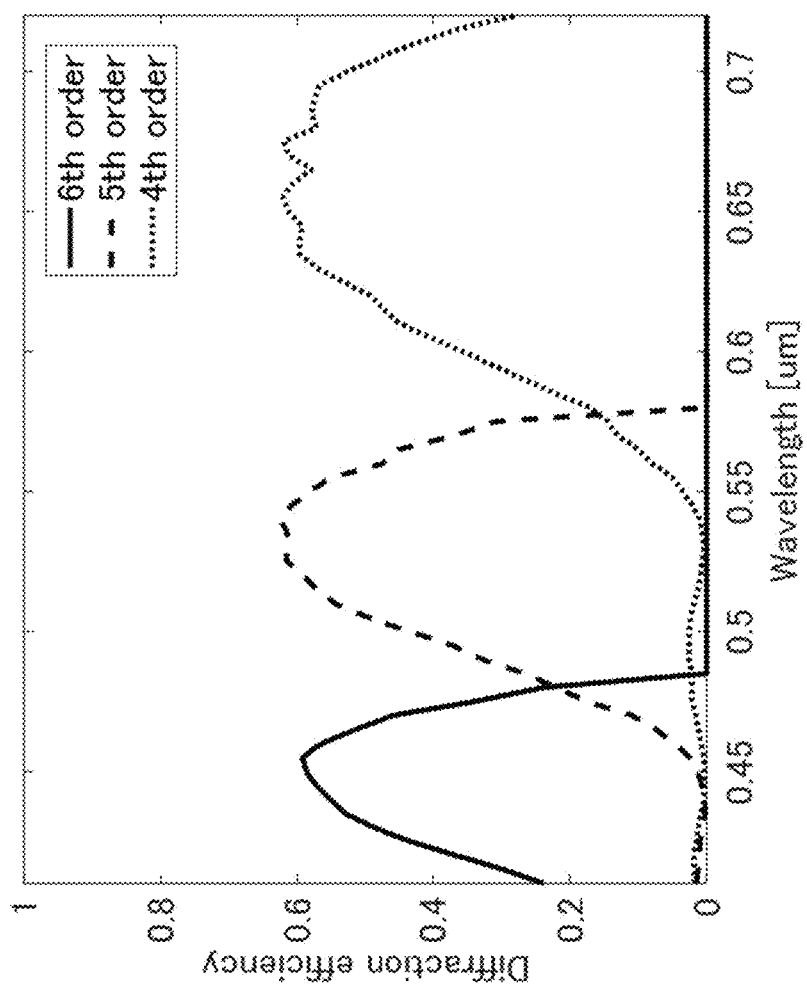
FIG. 18 is a diagram illustrating diffraction efficiency of a diffraction element according to at least the fourth embodiment.
Figure 19B:
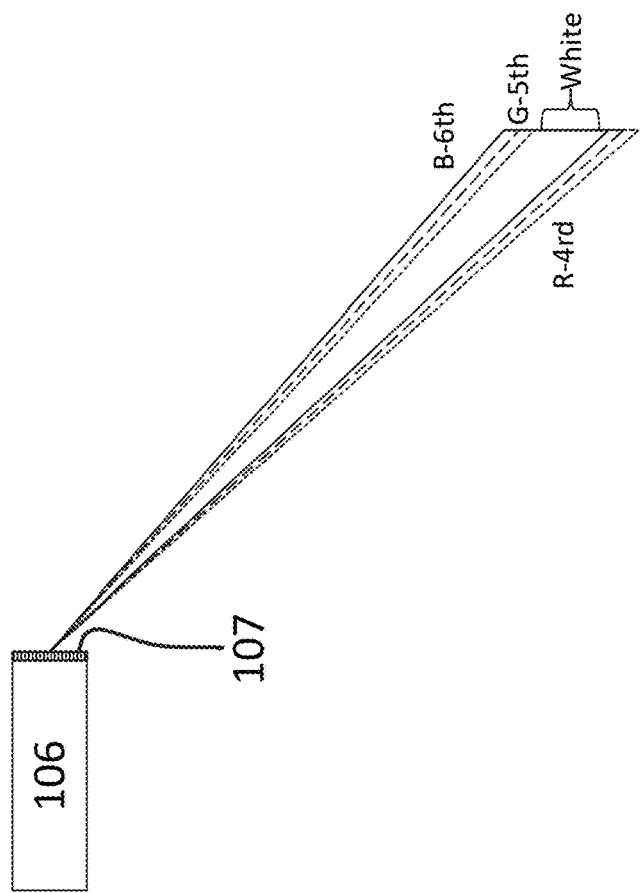
FIGS. 19A and 19B are schematic diagrams, where FIG. 19A describes illumination for acquiring monochrome images using first order diffracted light, and FIG. 19B describes illumination for acquiring color images using higher order diffracted light.
Figure 19A:
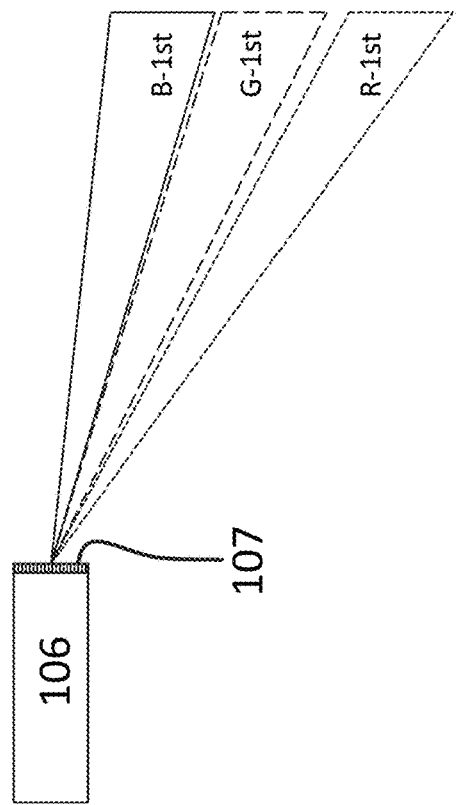

The diffraction element 107 disposed on the spacer 106 is described herein with reference to FIGS. 18 through 19B. FIG. 18 illustrates diffraction efficiency of the diffraction element 107, and FIGS. 19A and 19B illustrate formation of white illumination light by the diffraction element 107.

In a normal design, when white light enters the diffraction element 107, the subject is irradiated by a rainbow-color spectral sequence of diffracted light of one particular order. FIG. 19A is an example of using first-order diffracted light. Each location of the subject is irradiated by light of a certain one wavelength, and the reflectance of that wavelength is measured by the spectroscope 111. In SEE, illumination by such first-order diffracted light is sufficient to acquire a monochrome image.

In a case of acquiring a color image, reflectance information corresponding to the three primary colors of red, green, and blue are needed from the same position on the subject, so the method of using only first-order diffracted light cannot be applied in one or more embodiments. Reflected light for a certain location on the subject only has information of one wavelength (see e.g., FIG. 19A). Accordingly, a separate method is useful to acquire a color image in one or more embodiments.

Accordingly, higher-order diffraction light is used in one or more embodiments, as illustrated in FIG. 19B. The longer the wavelength is, the greater the diffraction angle is. Also, the higher-order the diffraction light is, the greater the diffraction angle is. Taking advantage of this, sixth-order diffracted light is used for blue (short wavelength), fifth-order diffracted light is used for green (mid-length wavelength), and fourth-order diffracted light is used for red (long wavelength). Appropriately selecting the pitch of the diffraction element 107 in doing so enables diffraction to be performed such that the fourth-order, fifth-order, and sixth-order diffracted lights are almost completely overlaid on the subject. This enables overlaying of a blue spectral sequence, green spectral sequence, and red spectral sequence, on the subject, to form illumination light of spectral sequences equivalent to white light.

In a case of using a diffraction grating such as shown in Table 1 as the diffraction element 107, settings can be made where high diffraction efficiency is obtained, with sixth-order diffracted light around 415 to 475 nanometers, fifth-order diffracted light around 498 to 570 nanometers, and fourth-order diffracted light around 622 to 712 nanometers, as illustrated in FIG. 18. Setting a diffraction grating formed in this way as the diffraction element 107 enables a spectral sequence of white light on the subject to the obtained.

TABLE 1

Parameters of Diffraction Grating 107 in at least a Fourth Embodiment

| | |
|---|---|
| Pitch | 1.54 microns |
| Duty ratio | 0.75 |
| Depth | 1.88 microns |
| Refractive index | 1.50 |

Figure 20:
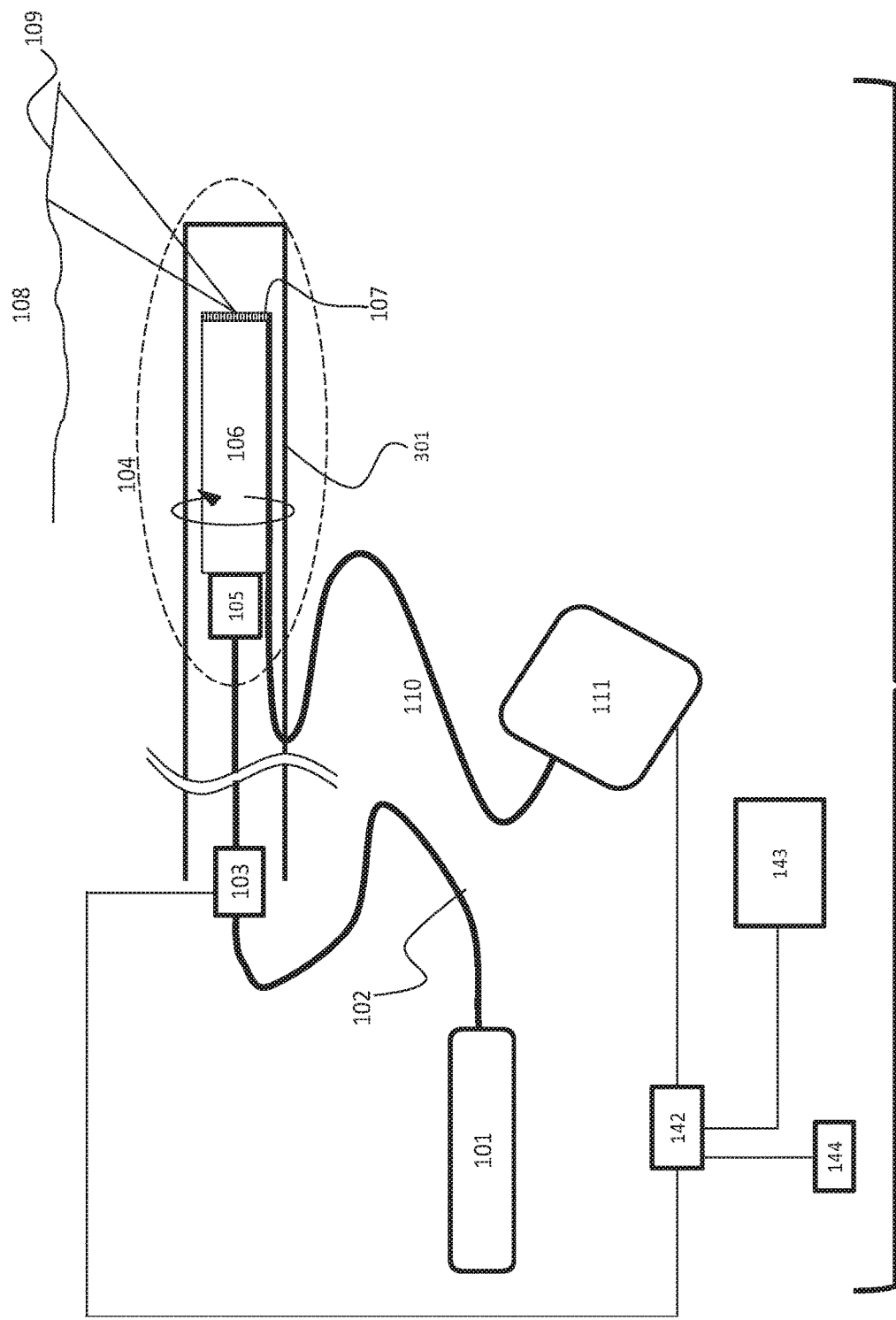
FIG. 20 is a schematic diagram describing an endoscope system according to at least a fifth embodiment.

An image processing circuit 142 (see e.g., embodiment examples of the image processing circuit 142 in at least FIGS. 14, 15, 20, etc.) converts spectral information (relationship between wavelength and light intensity) that the computing unit 208 of the spectroscope 111 has obtained into reflected light intensity for each position on the subject (more accurately, each angle of light emitted from the diffraction element 107). In one or more embodiments, the image processing circuit 142 may comprise or be part of a computer, such as the computer 1200 or the computer 1200' discussed further below. Theoretical calculation regarding diffraction may be used for this calculation, or a relationship between actually-measured wavelength and subject position may be used.

In the case of the illumination for a monochrome image illustrated in FIG. 19A, one reflection intensity is obtained for each position on the subject. In the case of the illumination for a color image illustrated in FIG. 19B, three reflection intensities of red, green, and blue, are obtained for each position on the subject (i.e., RGB color information is obtained).

Further, the image processing circuit 142 generates a two-dimensional image from multiple reflection intensities obtained by scanning the spectral sequence 109. Rotating the portion from the RJ 103 to the light irradiation or probe unit 104 with the longitudinal direction of the light irradiation or probe unit 104 as the rotational axis scans the spectral sequence 109 over the subject 108 in a rotating manner. The image processing circuit 142 sequentially reads out the spectral information that the computing unit 208 has acquired as the spectral sequence 109 is being scanned, to obtain reflected light intensity for each position as described above. The image processing circuit 142 generates one two-dimensional image (reflectance information of the subject) by arraying the reflected light intensities so that the rotations of the light irradiation or probe unit 104 correspond to one image. The generated two-dimensional image may be subjected to orthogonal coordinate conversion, so that the generated image and shape of the subject are closer. The generated image is displayed on a display device 143 (or any other display device, including, but not limited to, the other display devices discussed herein), and also saved in memory 144 (or any other memory, including, but not limited to, the other memory components discussed herein).

An example of the light flux splitter 203, which is at least one feature of the present disclosure, has been described where light is split into four light fluxes, but the imaging optical system can be further reduced in size by splitting into more than four. It should be noted, however, that splitting into a greater number of light fluxes means light entering the imaging optical system at a greater angle, which should be handled carefully in one or more embodiments. For example, there is a possibility that cost may increase due to increasing the number of lenses for imaging capabilities at greater angles, so the optimal number of light fluxes into which the light is split should be selected in accordance with the desired wavelength resolution.

Further, the light flux splitter 203 may be configured using a prism instead of mirrors. The light fluxes split by the light flux splitter 203 are not restricted to parallel light fluxes, and may be light fluxes having curvature.

Moreover, the line sensors 207-1 through 207-4 may be replaced by a single area sensor in one or more embodiments. An area sensor is an arrangement where photoreceptors are two-dimensionally arrayed, and a CCD image sensor, CMOS image sensor, and so forth, can be used. Spectral information and two-dimensional images can be acquired in the same way as using line sensors, by reading and computing output values of pixels of the area sensor situated at the same positions as the pixels of the line sensors 207-1 through 207-4.

A fifth embodiment is described herein with reference to FIG. 20. The fifth embodiment is an endoscope using the system described in at least the fourth embodiment.

The light irradiation or probe unit 104 is inserted into a sheath 301 that is transparent with regard to the measurement wavelength bands, and the light irradiation or probe unit 104 rotates within the sheath 301 (the sheath portion does not rotate). Thus, the light irradiation or probe unit 104 can be inserted into the body cavity, and two-dimensional images within the body cavity can be obtained by the method described in at least the fourth embodiment.

The light irradiation or probe unit 104 from the RJ 103 toward the distal end, and the sheath 301, can be removed and exchanged. The light irradiation or probe unit 104 and sheath 301 that have been inserted into the body can be removed and discarded, and a new light irradiation or probe unit 104 attached, to eliminate the cleaning process.

This endoscope is configured using optical fiber for illumination and optical fiber for detection, and accordingly it is at least one feature thereof that an endoscope that is extremely slender, around one millimeter in diameter, can be configured. Thus, application of the endoscope is not restricted to digestive organs, where endoscopes are normally used, but application can also be made to other various parts of the body, such as circulatory organs, respiratory organs, urinary organs, and so forth.

Figure 21:
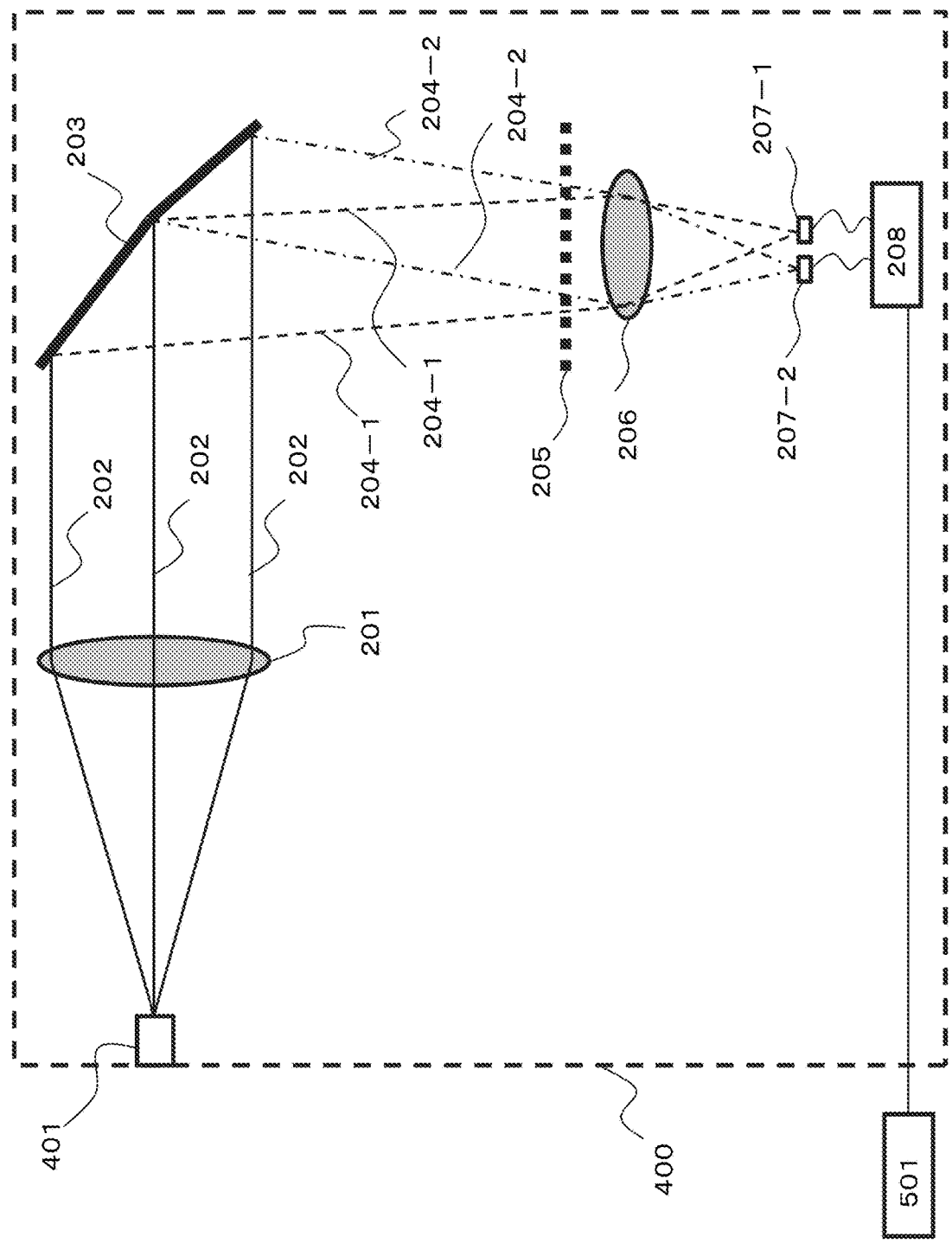
FIG. 21 is a schematic diagram describing a spectral apparatus according to at least a sixth embodiment.

A sixth embodiment is described herein with reference to FIG. 21. One or more embodiments of the present disclosure are not restricted to the SEE spectroscope described in at least the fourth embodiment, and can be used as a spectral apparatus that measures wavelength spectra of light. A spectral apparatus 400 (which may be part of the spectrometer 111) guides in light of which the wavelength spectrum is to be measured, using a light input unit 401. In a case of guiding in light using a fiber, a fiber port can be used as the light input unit 401. In a case of guiding in light propagating through the air, a pinhole or slit, and a lens or mirror to collect light thereto, are used as the light input unit 401. Light emitted from the light input unit 401 is subjected to the method described in the fourth embodiment, to obtain light intensity (wavelength spectrum) for each wavelength of input light at the computing unit 208. A calculator 501 reads in the spectral information that the computing unit 208 has acquired, and displays a wavelength spectrum on a monitor that is omitted from illustration. The calculator 501 also records the wavelength spectrum in a recording medium that is omitted from illustration. The calculator 501 and/or the computing unit 208 may be included in or comprise a computer, in one or more embodiments, such as, but not limited to, the computer 1200, the computer 1200', etc. as discussed further below.

The present disclosure is applicable to an image acquisition apparatus that forms images with high light usage efficiency at a low cost.

Figure 22:
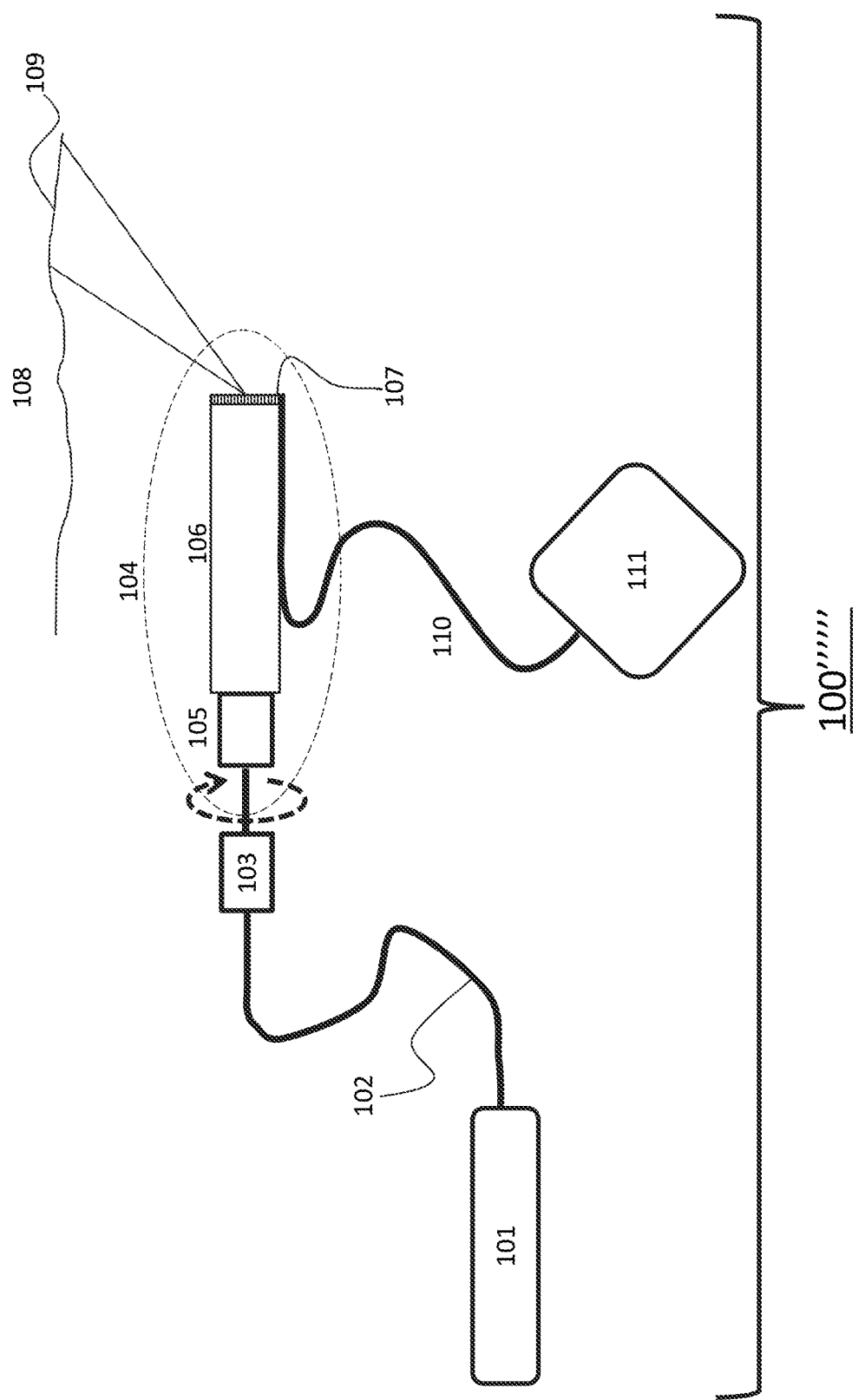
FIG. 22 is an SEE system according to at least a seventh embodiment.
Figure 23:
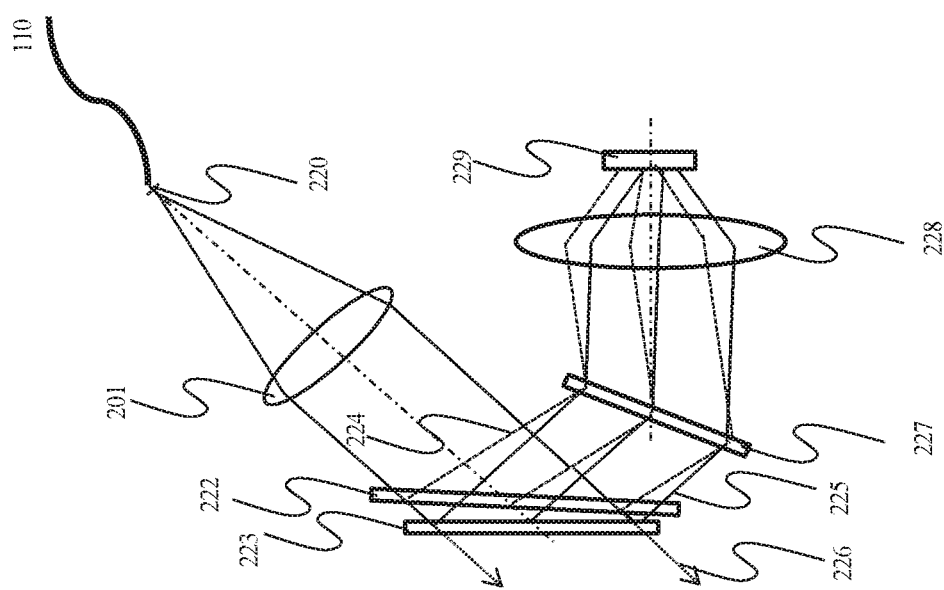
FIG. 23 is an optical cross-sectional view of a spectroscope according to at least the seventh embodiment.
Figure 24B:
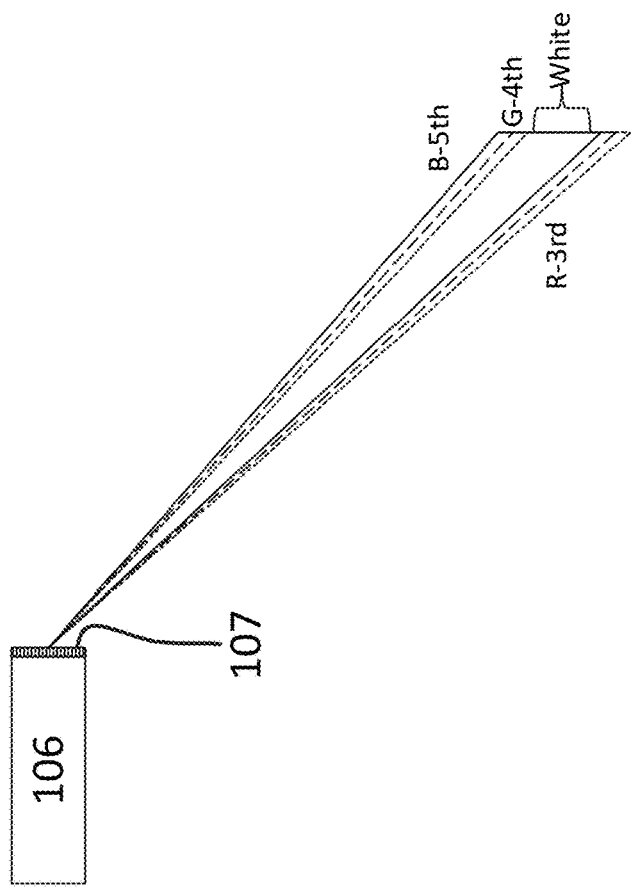
FIGS. 24A and 24B are schematic views for describing white light illumination of a diffraction element according to at least the seventh embodiment.
Figure 24A:
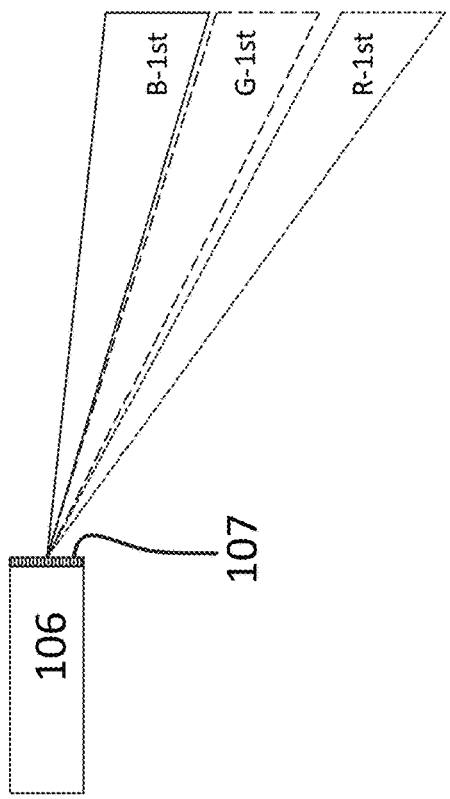
Figure 25:
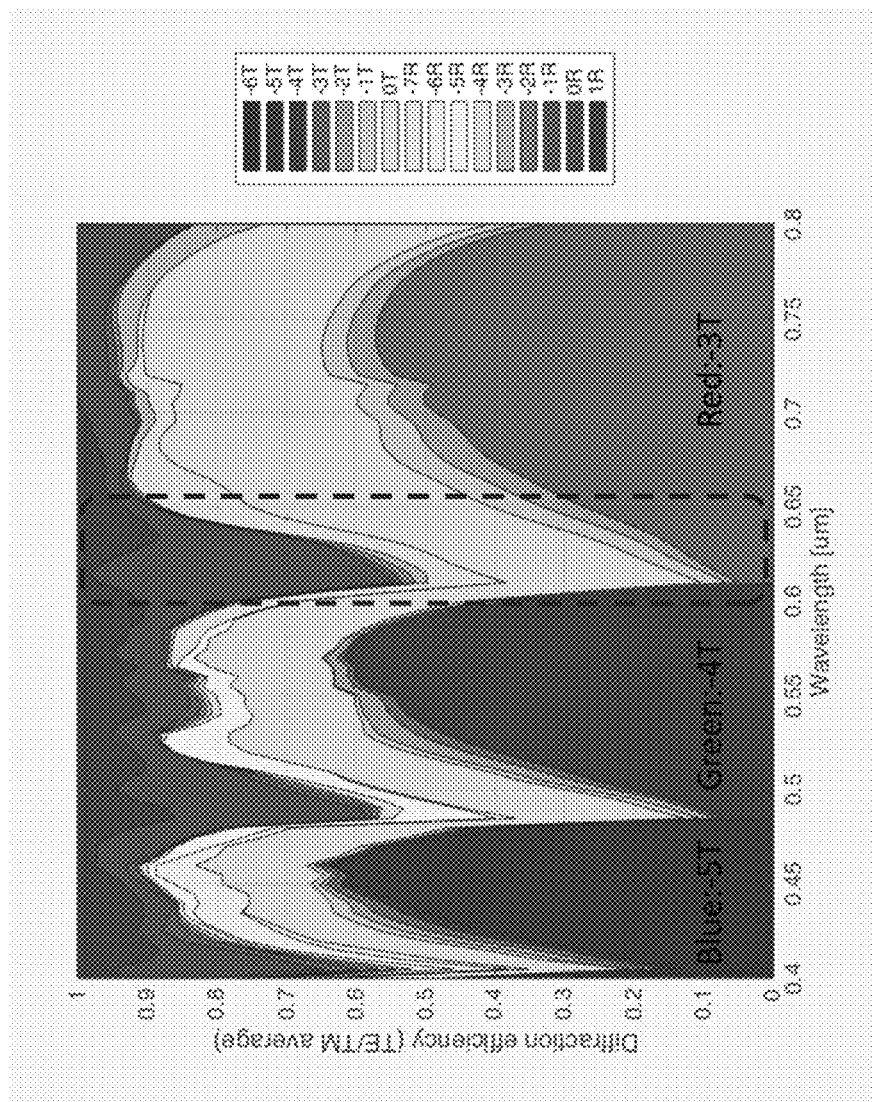
FIG. 25 is a diagram illustrating a diffraction efficiency of the diffraction element disposed in a probe portion according to at least the seventh embodiment.
Figure 26:
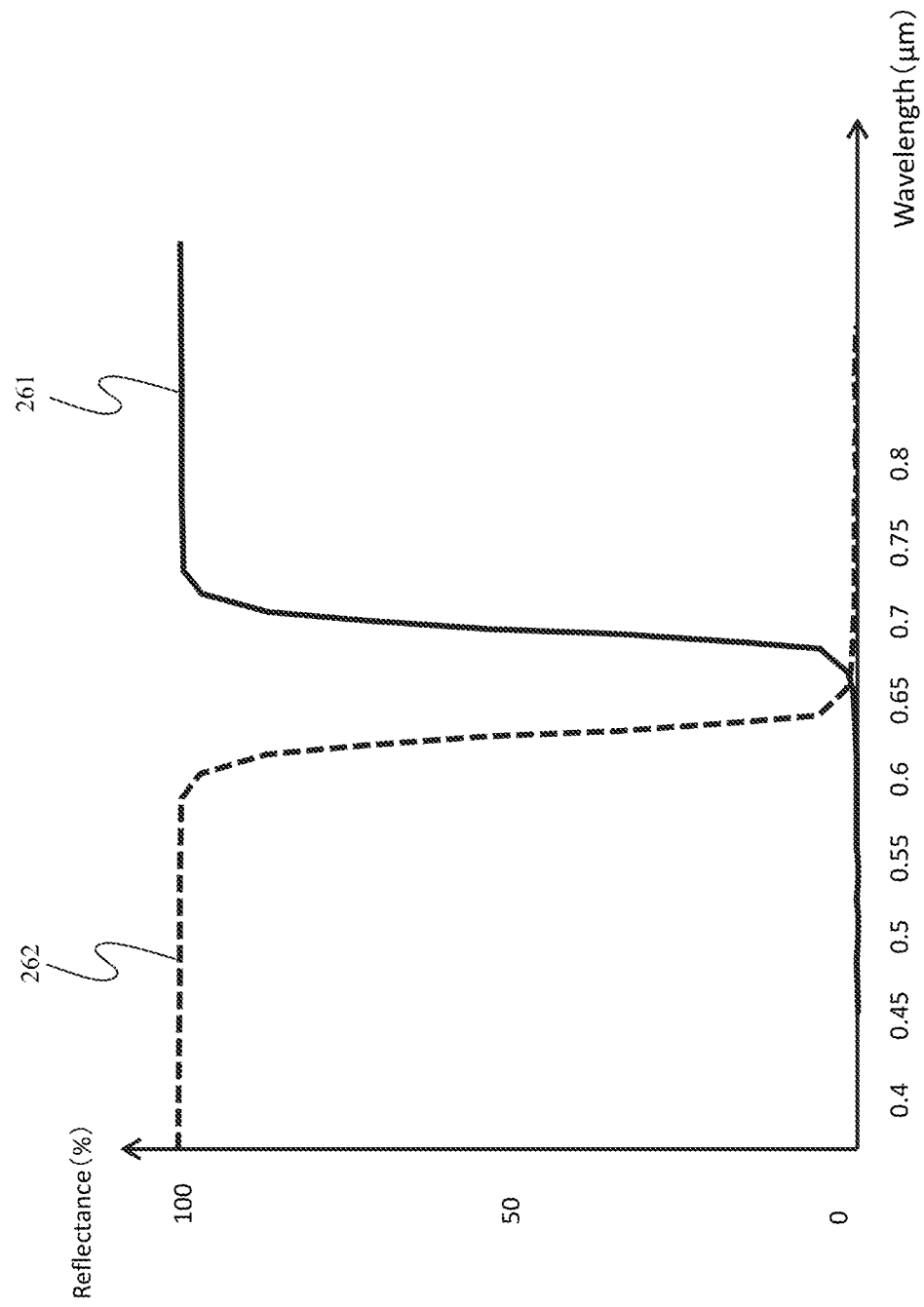
FIG. 26 is a diagram illustrating spectral characteristics of dichroic mirrors according to at least the seventh embodiment.
Figure 28A:
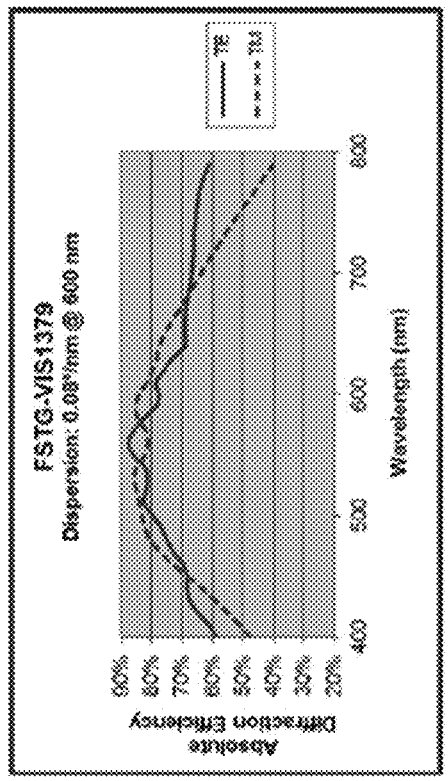
FIGS. 28A and 28B are diagrams illustrating an incident angle characteristic of a diffraction grating according to at least the seventh embodiment.
Figure 28B:
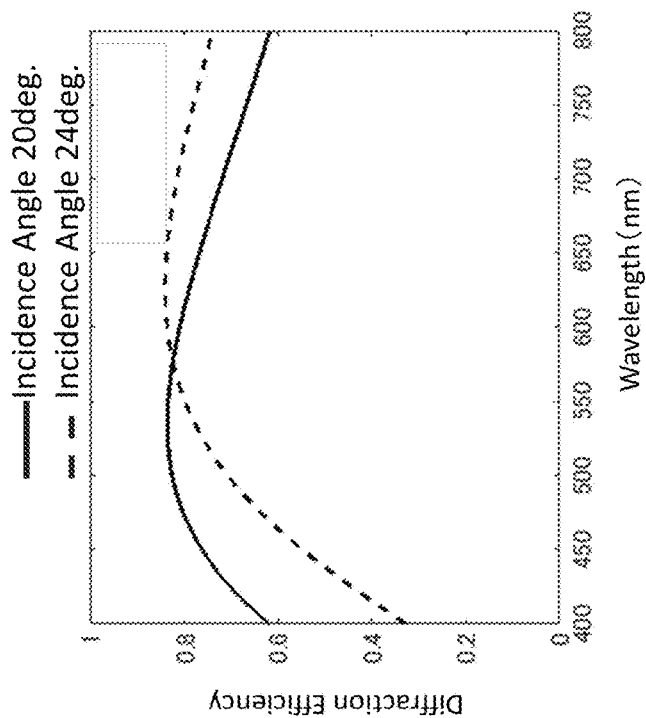

Referring to FIGS. 22 to 28B, a seventh embodiment of the present disclosure is described herein. FIG. 22 illustrates an entirety of an SEE system including a spectroscope according to the present embodiment, and FIG. 23 illustrates an optical cross-section of the spectroscope installed inside the SEE system. FIGS. 24A and 24B illustrate a state in which white illumination light is formed with a diffraction element, FIG. 25 illustrates the diffraction efficiency of the diffraction element of a probe portion, and FIG. 26 illustrates an example of wavelength characteristics of dichroic mirrors installed inside the spectroscope. FIGS. 27A to 27C are diagrams illustrating an arrangement of a spectral sequence spectrally dispersed on an image pickup element with a diffraction grating, and FIGS. 28A and 28B are diagrams illustrating an incident angle characteristic of the diffraction grating.

In at least the embodiment of FIG. 22, light emitted from a white light source 101 is transmitted through an illumination light transmission fiber 102, and enters a probe portion 104 through a rotary junction (hereinafter, referred to as an RJ) 103. In the probe portion 104, a white luminous flux enters a spacer 106 through a gradient index lens (hereinafter, referred to as a GRIN lens) 105. A diffraction element 107 is formed at the distal end of the spacer 106. The white luminous flux incident on the diffraction element 107 forms a spectral sequence 109 on a testee 108. Reflected light from the spectral sequence 109 is captured by a detection fiber 110. Although the detection fiber 110 in FIG. 22 is formed of a single fiber, a plurality of fibers may be used. The light captured by the detection fiber 110 is diffracted and detected with a spectroscope 111 provided on an exit side of the detection fiber 110. Additionally or alternatively, any of the detection fiber(s) 110 and/or any of the spectrometers 111 discussed herein may have the configuration(s) as shown in FIG. 1B and FIG. 1C as discussed above. In the above, by rotating a portion from the RJ 103 to the probe portion 104 about a rotation axis extending in a longitudinal direction of the probe portion 104, the spectral sequence 109 moves in a direction orthogonal to the sequence, such that reflectance information in two-dimensional directions can be obtained. By aligning the above, a two-dimensional image can be formed.

FIG. 23 is an optical cross-sectional view of the spectroscope 111 of the present embodiment. The luminous flux emitted from a fiber end 220 of the detection fiber 110 is converted into a parallel luminous flux with a collimator 201, and is incident on dichroic mirrors 222 and 223. The dichroic mirror 222 has a spectral characteristic of reflecting a red wavelength, and transmitting a blue to green wavelength. On the other hand, the dichroic mirror 223 has a spectral characteristic of reflecting the blue to green wavelength, and transmitting an orange to red wavelength. A luminous flux 224 in the red band and a luminous flux 225 in the blue to green band, that is, the two wavelength bands that have been separated with the dichroic mirrors 222 and 223, enter a diffraction grating 227 at different angles. The luminous fluxes 224 and 225 that have been diffracted by the diffraction grating 227 are formed into an image on a one-dimensional image pickup element 229 with an imaging optical system 228. The luminous flux 224 in the red band and the luminous flux 225 in the blue to green band are converted into electric signals, or into optical intensity information of each wavelength, with the one-dimensional image pickup element 229. A two-dimensional image can be formed by temporally detecting the optical intensity information in accordance with the shifting of the spectral sequence 109. Note that the luminous flux 226 in the orange band that has transmitted through the dichroic mirror 223 does not reach the image pickup element 229. The spectral characteristic of the dichroic mirror(s) 222 and 223 will be described later in more detail.

Portion Related to Present Disclosure that Describes Colorization of SEE by Using Higher Order Diffraction Light in Diffraction Element Disposed at Distal End of Probe Referring next to FIGS. 24A to 25, the diffraction element 107 for at least this embodiment provided on the spacer 106 will be described. Normally, when a white light enters the diffraction element, a rainbow-colored spectral sequence is formed with one order diffraction light. In the SEE, when the acquired image is monochrome, no issue is caused by the illumination of the above one order diffraction light. However, when a color image is acquired, reflectance information corresponding to the three primary colors, that is, red, green, and blue, is needed from the same position on the testee. Note that in the method using the one order diffraction light alone, the reflected light from a certain position on the testee has information of only one wavelength (FIG. 24A). Accordingly, in the method using the one order diffraction light alone, another method may be needed to acquire a color image. Accordingly, as illustrated in FIG. 24B, higher order diffraction light is used. In diffraction, the diffraction angle becomes larger as the wavelength becomes longer. Furthermore, as the order of the diffraction light becomes higher, the diffraction angle becomes larger. Using the above, five order diffraction light is used in blue (short wavelength), four order diffraction light is used in green (intermediate wavelength), and third order diffraction light is used in red (long wavelength), for example. In the above, by appropriately selecting the pitch of the diffraction element 107, the beams of three, four, and five order diffraction light can be diffracted to substantially overlap each other on the testee. By so doing, the blue spectral sequence, the green spectral sequence, and the red spectral sequence are overlapped on the testee, and illumination light of the spectral sequence corresponding to white light can be formed.

An issue encountered when using the higher order diffraction light is the diffraction efficiency. In a case in which an amplitude diffraction grating is used as the diffraction element 107, the one order diffraction light has the highest diffraction efficiency, and the diffraction efficiency decreases as the order becomes higher. Conversely, in a case in which a phase diffraction grating is used, by appropriately selecting the grating height of the diffraction grating and the refractive index of the base material, the diffraction efficiency of the higher order diffraction light can be improved. For example, a case in which a phase diffraction grating illustrated in Table 2 is used as the diffraction element 107 will be described in FIG. 25. In FIG. 25, the axis of ordinates is the diffraction efficiency, and the axis of abscissas is the wavelength. The numerical values in the legend denote the diffraction orders, T denotes transmitted diffraction light, and R denotes reflect diffraction light. In the diagram, Blue:−5T denotes transmitted −five order diffraction light in a blue wavelength band. As described above, settings can be made such that the five order diffraction light is most efficient around 408 to 468 nm, the four order diffraction light is most efficient around 510 to 585 nm, and the third order diffraction light is most efficient around 680 to 780 nm. By configuring the diffraction grating with such a shape to serve as the diffraction element 107, a spectral sequence that is to become white light can be obtained on the testee.

TABLE 2

Parameters of Diffraction Element 107 in Seventh Embodiment

| | |
|---|---|
| Pitch (μm) | 1.25 |
| Duty Factor | 0.8 |
| Depth (μm) | 1.7 |
| Refractive Index | 1.50 |

The reflectance information obtained in the above manner is converted into intensity information with the spectroscope 111, and an image is formed. Note that a color image can be formed by overlapping the intensity information corresponding to the three primary colors, namely, red, green, and blue. The resolution of the color image depends on the wavelength resolution of the spectroscope 111 regarding red, green, and blue, and the resolution becomes higher as the wavelength resolution becomes higher. However, issues may be encountered as follows:

(a) The human eyes are sensitive to the resolution in the green wavelength band, and among red, blue, and green, when the resolution of green is high, it looks as if the resolution is high. However, when the optical system inside the spectroscope 111 is configured in a particular manner, owing to the physical characteristic of the diffraction, the red area may become large on the image pickup element. As a result, the resolution of red becomes the highest and the resolution of green becomes low compared with that of red.

(b) In a case in which higher order diffraction light is used, an area (a broken line area in FIG. 25) with significantly low diffraction efficiency appears between areas corresponding to blue, green, and red with high diffraction efficiencies. Note that an area with low diffraction efficiency refers to an area with a diffraction efficiency that is half or smaller than half of the highest diffraction efficiency in the blue, green, and red areas. In a case in which the optical system inside the spectroscope 111 is configured in the particular manner discussed above in issue (a), the area on the image pickup element corresponding to the above area may be an extremely dark image. Accordingly, in such a situation, the above pixels of the above area will be wasted and the ultimate resolution will be lowered.

As one or more measures for the above issues and in order to improve the resolution of the acquired image without reducing the utilization efficiency of the acquired light, as illustrated in FIG. 23, a plurality of dichroic mirrors 222 and 223 are provided in the optical path that guides the light reflected by the testee to the image pickup element 229 of the spectroscope, the light is made to enter the diffraction grating 227 at different incident angles while optimizing the wavelength band that is used, and an image is formed on the image pickup element 229 by aligning spectral sequences in two bands with the imaging optical system 228 with practically no gap between the spectral sequences.

Referring to FIGS. 26 to 28B, details are described herein for one or more embodiments. FIG. 26 illustrates spectral characteristics of the two dichroic mirrors 222, 223. The axis of ordinates is the reflectance, and the axis of abscissas is the wavelength. Reference numeral 261 represents the spectral characteristic of the dichroic mirror 222 and reference numeral 262 represents the spectral characteristic of the dichroic mirror 223. The dichroic mirror 222 has the spectral characteristic of reflecting the red wavelength, and transmitting the blue to green wavelength. On the other hand, the dichroic mirror 223 has the spectral characteristic of reflecting the blue to green wavelength, and transmitting the orange to red wavelength. The luminous flux that is in the area in which the diffraction efficiency of the diffraction element of the probe portion is substantially low and that corresponds to a wavelength of 590 nm to 660 nm (orange to red on the short wavelength side) illustrated in FIG. 25 transmits through the dichroic mirror 223, and does not reach the diffraction grating 227. Furthermore, the two dichroic mirrors 222, 223 are inclined by about 2° with respect to each other, and the angles incident to the diffraction grating 227 are different by about 4°.

Referring to FIGS. 27A to 27C, the spectral sequences of the luminous flux 224 in the red band and the luminous flux 225 in the blue to green band that have been diffracted by the diffraction grating 227 are described herein. In a case in which white light enters the diffraction grating 227, a spectral sequence 601 illustrated in FIG. 27A appears. The axis of abscissas is the wavelength. The luminous fluxes reflected by the two dichroic mirrors 222, 223 are, as illustrated in FIG. 27B, formed of a spectral sequence 601a in the blue to green wavelength region, and a spectral sequence 601b in the red wavelength region, and the wavelength of 590 nm to 660 nm is lacking. FIG. 27C illustrates a state in which the luminous flux 224 in the red wavelength region and the luminous flux 225 in the blue to green wavelength region are formed into an image on the image pickup element 229 with the imaging optical system 228. Reference numeral 229a is a pixel of the image pickup element 229. The pixel has a strip shape that has a narrow width in a spectral direction. Since the two luminous fluxes 224, 225 are at an angle of about 4°, the parameters of each optical system are selected so that the gap between the two spectral sequences 601a, 601b is covered. For example, the pixel width of the image pickup element 229a is 12 μm, the pixel number is 2048, and the focal point distance of the imaging optical system 228 is 46.6 mm. Assuming that a wavelength range corresponding to blue to green is 408 to 585 nm, and a wavelength range corresponding to red is 680 to 780 nm, then, center wavelengths of the wavelength ranges are 495 nm and 730 nm. Regarding the diffraction angle of the center wavelength of each wavelength range, the diffraction angle of the wavelength 495 nm is –20° (incident angle 20°), and the diffraction angle of the wavelength 730 nm is –36.5° (incident angle 24°). In other words, it can be understood that there are scarcely no pixels that are not used and that become wasted in one or more embodiments of the present disclosure.

Table 3 illustrates parameters of the diffraction grating 227 manufactured by Ibsen Photonics A/S used in the present embodiment.

TABLE 3

Parameters of Diffraction Grating 207

| | |
|---|---|
| Pitch (μm) | 0.725 |
| Duty Factor | 0.9 |
| Depth (μm) | 2.5 |
| Refractive Index | 1.458 |

Furthermore, FIG. 28A illustrates the spectral characteristics of the diffraction efficiencies in a case in which a TE wave and a TM wave are made to enter the diffraction grating 227 at an incident angle of 20°. The incident angle 20° is a designed value for using the present diffraction grating in a wavelength band ranging from the visible to near infrared.

FIG. 28B illustrates spectral characteristics of average diffraction efficiencies of a TE wave and a TM wave in a case in which the incident angles are 20° and 24°. For example, the dichroic mirror 222 reflects the red wavelength so that the incident angle against the diffraction grating 227 is 24°, and the dichroic mirror 223 reflects the blue to green wavelength so that the incident angle against the diffraction grating 227 is 20°. As it is apparent from FIG. 28B, the diffraction efficiency of the red band in a case in which the incident angle is 24° is higher than a case in which the incident angle is 20°. An appropriate selection of the angles of the dichroic mirrors not only enables the wasted area of the spectral sequence formed as an image on the image pickup element 229 to be eliminated but also enables a high diffraction efficiency to be maintained in all of the wavelength bands.

The present embodiment is summarized as follows:

(a) By providing wavelength band splitting elements so that an area with a low diffraction efficiency is not guided onto the image pickup element, wasted pixels on the image pickup element can be reduced to the extent possible and the resolution can be improved. Specifically, compared with a case in which a spectral sequence of 408 nm to 780 nm is formed, as it is, as an image on the image pickup element, the resolution can be increased by 20 percent or more.

(b) By providing the wavelength band splitting elements so that the luminous fluxes enter the diffraction grating at appropriate angles, the diffraction efficiency can be improved and S/N of the spectroscope can be improved; accordingly, the resolution of the image can be improved. Specifically, for example, the overall diffraction efficiency in the red area can be improved and, in particular, the diffraction efficiency of 780 nm on the longest wavelength side can be improved to 75% from 63%.

Note that while an expression "low" diffraction efficiency is described herein, "low" refers to being lower than the highest value of the diffraction efficiencies in the diffraction orders. Moreover, it is desirable to be roughly under 50% of the peek value of the diffraction efficiency.

Furthermore, in the spectroscope of the present embodiment, the wavelength range corresponding to blue to green is 408 to 585 nm, and the wavelength range corresponding to red is 680 to 780 nm; however, the ranges are not limited to the above ranges. Considering a spectroscope used in an SEE device or system, it is desirable that the short wavelength side of the wavelength region of blue to green exceeds 400 nm. The above is because the transmittance of the material used in optical systems is lower in short wavelengths and sufficient signals cannot be obtained in the region in which the wavelength is shorter than 400 nm. Moreover, it is more desirable that the wavelength exceeds 405 nm since a higher transmittance can be obtained. Furthermore, it is desirable that the long wavelength side of the wavelength region of blue to green is under 600 nm. The above is because when used as an organism observation device in particular, it is highly probable that an appropriate reflection image cannot be obtained since the absorption spectrum of hemoglobin abundantly present inside the body steeply changes at around 600 nm. Moreover, it is desirable that the wavelength is under 590 nm. By so doing, a more accurate reflection image can be obtained. Furthermore, due to the same reason as the upper limit of the blue to green, the lower limit of the red wavelength region is desirably a wavelength longer than 600 nm. Moreover, it is desirable that the wavelength exceeds 620 nm. Furthermore, it is desirable that the upper limit of the wavelength is under 900 nm. The above is because in an Si-based sensor typically used as an image pickup element, when the wavelength is longer than 900 nm while the visible light region is given sufficient sensitivity, the sensitivity decreases at 900 nm or more. Moreover, when the upper limit is under 850 nm, a higher sensitivity can be obtained as a whole. That said, modifications to the subject wavelength ranges may be made in accordance with one or more aspects of the present disclosure.

Furthermore, in the present embodiment, an example has been illustrated in which the wavelength band splitting elements are provided to improve the diffraction efficiency in the red area; however, by appropriately selecting other angles, the diffraction efficiency of other wavelength regions can be improved.

As described above, in the configuration of an SEE device or system that obtains a color image by using the higher order diffraction light, by providing the wavelength band splitting elements so that the band of the diffraction element of the probe portion with a low diffraction efficiency is not guided to the image pickup element, wasted pixels on the image pickup element can be reduced to the extent possible and the diffraction efficiency of the diffraction grating of the spectroscope can be increased; accordingly, the resolution of the obtained color image can be improved.

Figure 29:
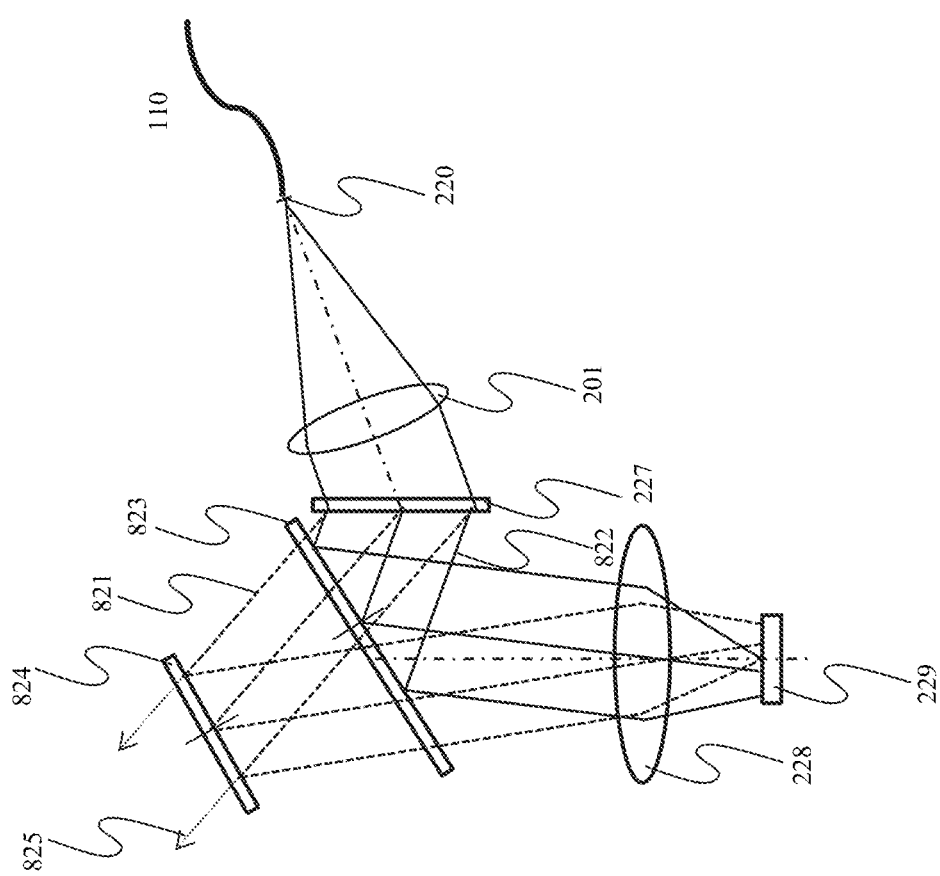
FIG. 29 is an optical cross-sectional view of a spectroscope according to at least an eighth embodiment.

Referring to FIG. 29, an eighth embodiment of the present disclosure is described herein. FIG. 29 illustrates an optical cross-section of a spectroscope according to the eighth embodiment installed inside the SEE system. In the eighth embodiment, the wavelength band splitting elements used in at least the seventh embodiment are disposed between the diffraction grating and an imaging lens. Members that are the same as those of the seventh embodiment are attached or associated with the same reference numerals.

A luminous flux emitted from the fiber end 220 of the detection fiber 110 is converted into a parallel luminous flux with the collimator 201, and enters the diffraction grating 227. Among the luminous fluxes diffracted by the diffraction grating 227, the orange to red wavelength is denoted by 821, and the blue to green wavelength is denoted by 822. The above luminous fluxes sequentially enter dichroic mirrors 823 and 824. The dichroic mirror 823 has a spectral characteristic of reflecting the blue to green wavelength, and transmitting the red wavelength. On the other hand, the dichroic mirror 824 has a spectral characteristic of reflecting the orange to red wavelength, and transmitting the blue to green wavelength. The spectral characteristics of the dichroic mirrors 823, 824 are similar to those characteristics in FIG. 26. Accordingly, the luminous flux that has been transmitted through the dichroic mirror 824 and that is in the orange to the red band having a relatively short wavelength, in other words, a luminous flux 825 that corresponds to the wavelength of 590 nm to 660 nm illustrated in FIG. 25 and that is in an area in which the diffraction efficiency of the diffraction element of the probe portion is substantially low does not reach the image pickup element 229.

Similar to the seventh embodiment, assuming that the wavelength range corresponding to blue to green is 408 to 585 nm, and the wavelength range corresponding to red is 680 to 780 nm, then the center wavelengths of the wavelength ranges are 495 nm and 730 nm, respectively. When entering the diffraction grating 227 at an incident angle of 20°, the diffraction angles of the center wavelengths are roughly about −20° and −42°. The two dichroic mirrors 823, 824 are inclined by about 3° with respect to each other, and the differences in the incident angles of the center wavelengths of the wavelength ranges against the imaging optical system 228 are compressed to about 22° to 16°. With the above, as illustrated in FIG. 27C, a luminous flux 821 in the red wavelength region and a luminous flux 822 in the blue to green wavelength region are formed with the imaging optical system 228 into an image that just covers the wavelength 590 nm to 660 nm that is the gap between the two spectral sequences on the image pickup element 229.

In the eighth embodiment, since the dichroic mirrors 823, 824 are disposed between the diffraction grating 227 and the imaging lens (e.g., the imaging optical system 228), advantageously, the inclinations of the dichroic mirrors 823, 824 can be changed freely. On the other hand, since the luminous flux that has been spectrally dispersed and scattered with the diffraction grating 227 enters the dichroic mirrors 823, 824, the spectroscope may become larger compared to that of the seventh embodiment.

As described above, in the configuration of an SEE device or system that obtains a color image by using the higher order diffraction light, by providing the wavelength band splitting elements so that the band of the diffraction element of the probe portion with a low diffraction efficiency is not guided to the image pickup element, wasted pixels on the image pickup element can be reduced to the extent possible and the resolution of the obtained color image can be improved.

Figure 30:
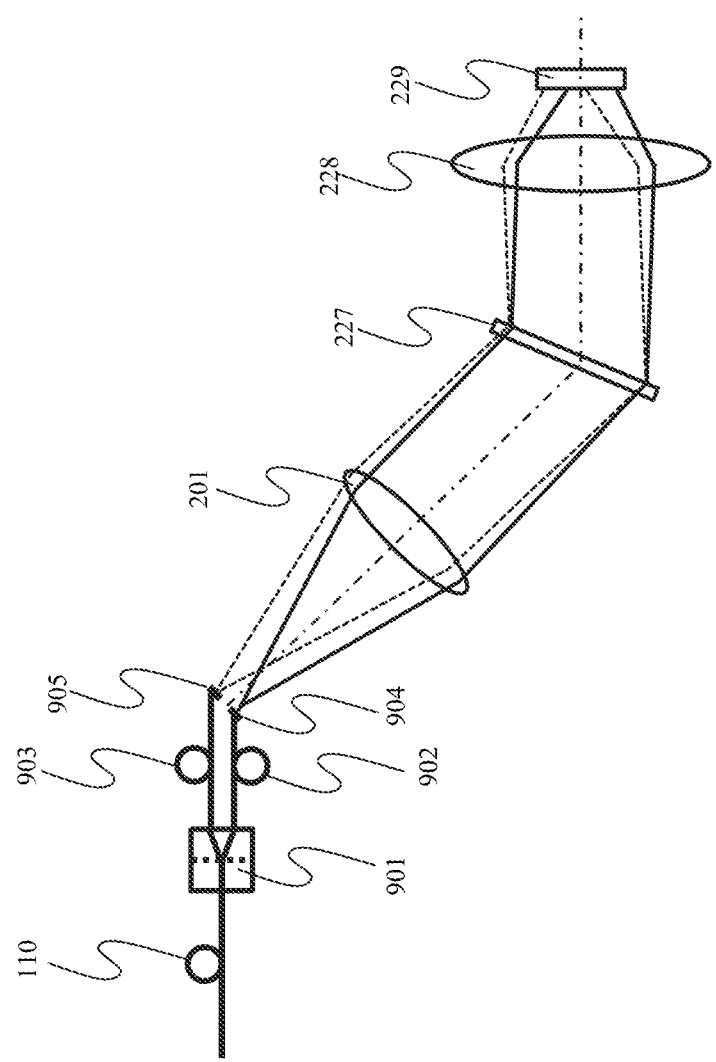
FIG. 30 is an optical cross-sectional view of a spectroscope according to at least a ninth embodiment.

Referring to FIG. 30, a ninth embodiment of the present disclosure is described herein. FIG. 30 illustrates an optical cross-section of a spectroscope according to the ninth embodiment installed inside the SEE system. In the ninth embodiment, instead of the dichroic mirrors used in the seventh embodiment, a wavelength separation filter is used as the wavelength band splitting element. Members that are the same as those of the seventh exemplary embodiment are attached or associated with the same reference numerals.

The luminous flux transmitted inside the detection fiber 110 enters a wavelength separation filter 901 and is separated into transmitted radiations in the blue to green wavelength and in the red wavelength.

Figure 31:
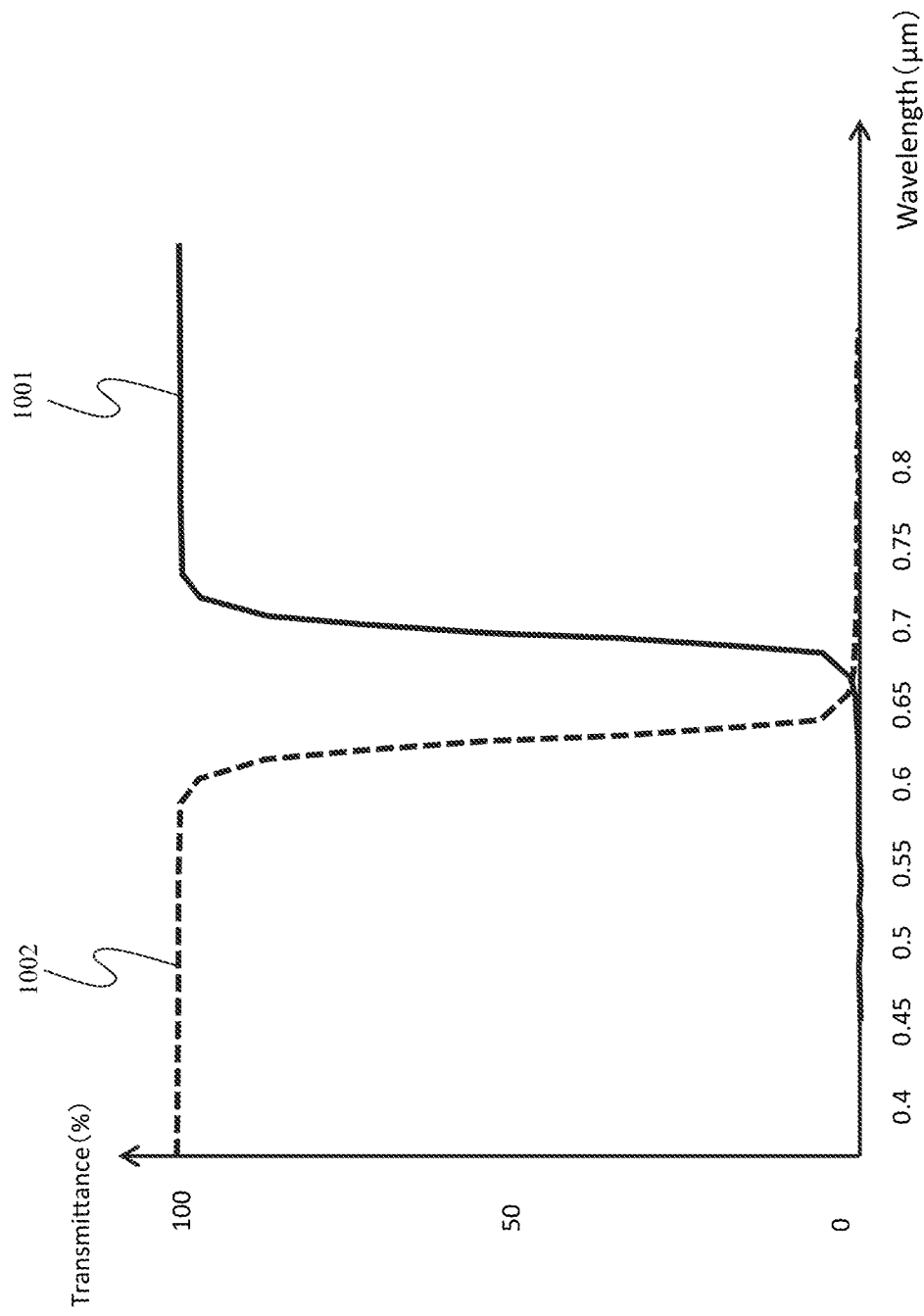
FIG. 31 is a diagram illustrating spectral characteristics of a wavelength separation filter according to at least the ninth embodiment.

FIG. 31 illustrates spectral characteristics of the wavelength separation filter 901. The axis of ordinates is the transmittance, and the axis of abscissas is the wavelength. Reference numerals 1001 and 1002 illustrate the spectral characteristics of the wavelength separation filter 901. The wavelength separation filter 901 separates the blue to green wavelength to a multimode fiber 902, and the red wavelength to a multimode fiber 903. On the other hand, in one or more embodiments, the wavelength separation filter 901 has a characteristic of not transmitting the luminous flux that is in the area in which the diffraction efficiency of the diffraction element of the probe portion is substantially low and that corresponds to a wavelength of 590 nm to 660 nm (orange to red on the short wavelength side) illustrated in FIG. 25.

The luminous fluxes emitted from multimode fiber ends 904 and 905 are converted into parallel luminous fluxes with the collimator 201, and enter the diffraction grating 227 at different angles. The multimode fiber ends 904 and 905 are disposed so as to be separated from each other at a predetermined distance, and similar to the seventh embodiment, the luminous flux in the blue to green wavelength enters the diffraction grating 227 at an incident angle of 20°, and the luminous flux in the red wavelength enters at an incident angle of 24°. For example, when the focal point distance of the collimator 201 is 116.5 mm, the multimode fiber ends 904 and 905 are disposed so as to be separated from each other at about 8 mm.

The luminous flux 224 in the red band and the luminous flux 225 in the blue to green band diffracted by the diffraction grating 227 are, as illustrated in FIG. 27B, formed of the spectral sequence 601a in the blue to green wavelength region, and the spectral sequence 601b in the red wavelength region, and the wavelength of 590 nm to 660 nm is lacking. As illustrated in FIG. 27C, the luminous flux 224 in the red wavelength region and the luminous flux 225 in the blue to green wavelength region are formed into an image on the image pickup element 229 with the imaging optical system 228. Since the two luminous fluxes are at an angle of about 4°, the parameters of each optical system are selected so that the gap between the two spectral sequences are covered. For example, the pixel width of the image pickup element 229a is 12 µm, the pixel number is 2048, and the focal point distance of the imaging optical system 208 is 46.6 mm. Assuming that a wavelength range corresponding to blue to green is 408 to 585 nm, and a wavelength range corresponding to red is 680 to 780 nm, then, center wavelengths of the wavelength ranges are 495 nm and 730 nm. Regarding the diffraction angle of the center wavelength of each wavelength range, the diffraction angle of the wavelength 495 nm is −20° (incident angle 20°), and the diffraction angle of the wavelength 730 nm is −36.5° (incident angle 24°). In other words, it can be understood that there are scarcely no pixels that are not used and that become wasted in one or more embodiments of the present disclosure.

Furthermore, as it is apparent from FIG. 28B, the diffraction efficiency in the red band in a case in which the incident angle is 24° is higher than a case in which the incident angle is 20°; accordingly, appropriate selection the focal point distance of the collimator and the dispositions of the multimode fiber ends not only enables the wasted area of the spectral sequence formed as an image on the image pickup element 229 to be eliminated but also enables a high diffraction efficiency to be maintained in all of the wavelength bands in one or more embodiments.

In the ninth embodiment, instead of dichroic mirrors disposed in the free space, the wavelength separation filter 901 provided in the fiber is used; accordingly, there is an advantage in that the optical system of the spectroscope can be configured in a compact manner. On the other hand, a costly wavelength separation filter is used as compared with the seventh embodiment.

As described above, in the configuration of an SEE device or system that obtains a color image by using the higher order diffraction light, by providing the wavelength band splitting element so that the band of the diffraction element of the probe portion with a low diffraction efficiency is not guided to the image pickup element 229, wasted pixels on the image pickup element 229 can be reduced to the extent possible and the diffraction efficiency of the diffraction grating 227 of the spectroscope can be increased; accordingly, the resolution of the obtained color image can be improved.

Figure 32:
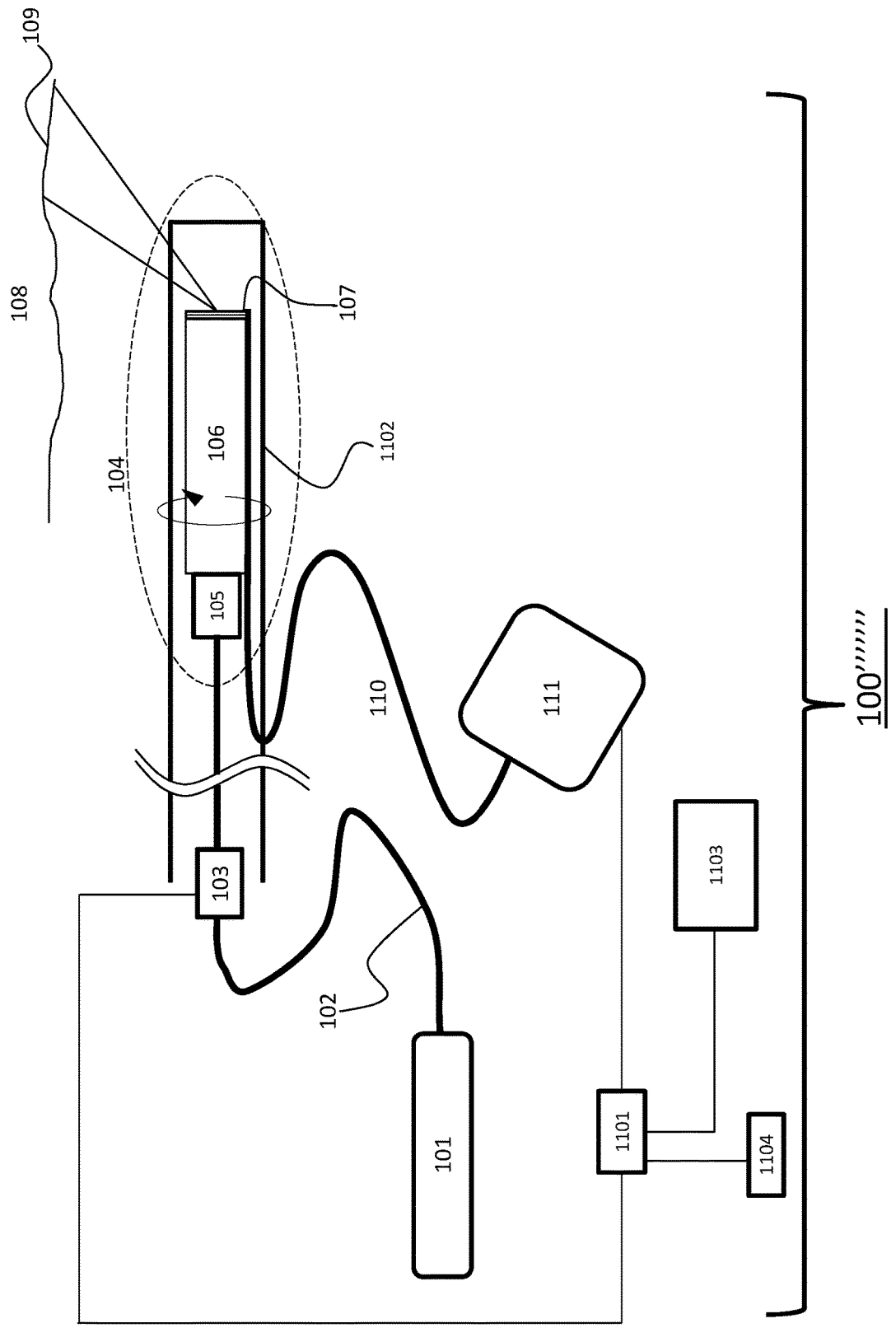
FIG. 32 is a diagram illustrating an endoscope system according to at least a tenth embodiment.

Referring to FIG. 32, a tenth embodiment of the present disclosure is described herein. The tenth embodiment is an endoscope using any one of the optical systems used in at least the seventh embodiment to the ninth embodiment. For example, in FIG. 23, the intensity information of the reflected and scattered light acquired with the one-dimensional image pickup element 229 is allocated to channels, namely, a blue (B) channel of the image, a green (G) channel, and a red (R) channel. The above information is processed as a single RGB pixel array with an image processing circuit 1101. In one or more embodiments, the image processing circuit 1101 may include or be a part of a computer, such as, but not limited to, the computer 1200, the computer 1200', the image processing circuit 142, etc. or other computing component(s) or device(s) discussed herein. In the above, the probe portion 104 is rotated about the longitudinal direction thereof and the information of the one-dimensional image pickup element 229 is sequentially read out so as to conform with or to the rotation. As the probe portion 104 rotates once, the pixel arrays that have been read out are aligned as a single image; accordingly, a color image is formed.

The formed image is displayed on a display device 1104 (or, alternatively or additionally, one of the other display devices discussed further below) and is stored in a memory 1103 (or, alternatively or additionally, one of the other memory component(s) discussed further below).

Since diffraction is performed using a high order diffraction, in the pixel number of each RGB channel on the image pickup element, red always has the largest pixel number and blue has the smallest pixel number. However, as described in at least the discussion of the seventh embodiment, due to the characteristics of the human eyes, the ultimate resolution of the image depends on the green resolution. Accordingly, at the image processing step, a compressing process that matches the pixel number of red to the pixel number of green is performed, and regarding the pixel number of blue, an interpolating process is performed by interpolation, so that ultimately, the image displayed on the display device 1104 is an image in which the pixel numbers of R, G, and B matches each other.

In the measured wavelength band, the probe portion 104 is inserted inside a transparent sheath 1102 (which in one or more embodiments may be the same as or similar to the sheath 301 discussed above), and is rotated inside the sheath 1102 (the sheath portion 1102 preferably does not rotate in one or more embodiments). The probe portion 104 can be used as an endoscope by, while rotating the probe portion 104, inserting the sheath portion 1102 into a body cavity.

Note that the probe portion 104 and the sheath 1102 from the RJ 103 to the end of the probe portion 104 and/or the sheath 1102 can be dismounted and replaced. After inserting the probe portion 104 and the sheath 1102 inside a body, the probe portion 104 and the sheath 1102 can be dismounted and discarded, and a new probe portion 104 can be mounted; accordingly, the washing process may be omitted or streamlined.

Since the present endoscope is configured of or includes an optical fiber for illumination and a detection fiber, an extremely fine endoscope of about φ1 mm can be fabricated, which is at least one of the many features of the present endoscope embodiment. Accordingly, the endoscope can be used not only in digestive organs in which endoscope is used frequently, but can be used in various regions as well, such as the circulatory organs, the respiratory organs, and the urinary organs.

Figure 33:
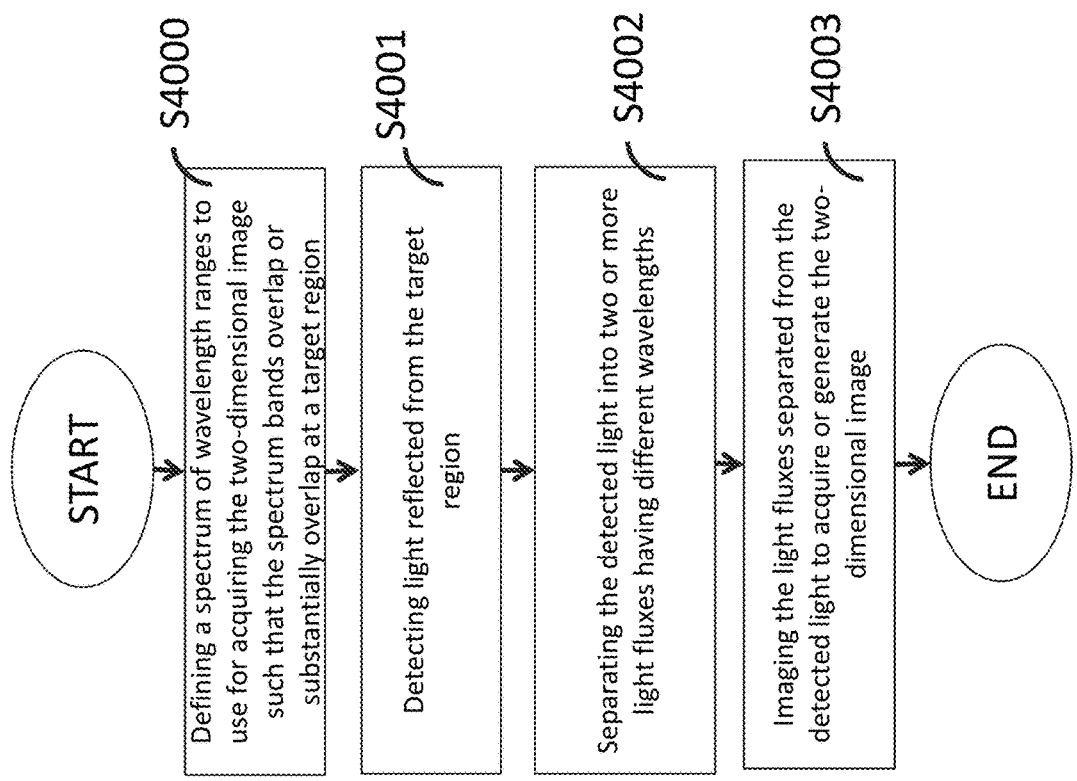
FIG. 33 is a flow diagram showing a method of performing an imaging technique in accordance with one or more aspects of the present disclosure.

In accordance with one or more aspects of the present disclosure, one or more methods for performing imaging are provided herein. FIG. 33 illustrates a flow chart of at least one embodiment of a method for performing imaging. Preferably, the method(s) may include one or more of the following: (i) defining a spectrum of wavelength ranges to use for acquiring the image such that the spectrum bands overlap or substantially overlap on a sample or target (see step S4000 in FIG. 33); (ii) detecting light reflected from the target region (see step S4001 in FIG. 33); (iii) separating the detected light into two or more light fluxes having different wavelengths (see step S4002 in FIG. 33); and imaging the light fluxes separated from the detected light to acquire or generate the black and white and/or color image (see step S4003 in FIG. 33). One or more methods may further include at least one of: using a probe grating to generate the spectrum bands that overlap or substantially overlap on the target region; and optimizing the probe grating so that a diffraction efficiency is high within the wavelength ranges. In one or more embodiments, a SEE probe may be connected to one or more systems (e.g., the system 100, the system 100', the system 100", the system 100'", the system 100"", the system 100'"", the system 100"""", the system 100'"""", etc.) with a connection member or interface module. For example, when the connection member or interface module is a rotary junction for a SEE probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the SEE probe may be separate from the detection portion of the SEE probe. For example, in one or more applications, a probe may refer to the illumination assembly, which includes the illumination fiber 102 (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: the detection fiber 110, the spectrometer 111, the computer 1200, the computer 1200', the image processing circuit 142, the image processing circuit 1101, etc. The detection fibers, such as the detection fiber(s) 110, may surround the illumination fiber, such as the IF 102, and the detection fibers may or may not be covered by the grating, such as the grating 107.

Unless otherwise discussed herein, like numerals indicate like elements. For example, while variations or differences exist between the systems, such as, but not limited to, the system 100, the system 100', the system 100", the system 100'", the system 100"", the system 100'"", the system 100"""", the system 100'"""", etc., one or more features thereof may be the same or similar to each other, such as, but not limited to, the light source 101 or other component(s) thereof (e.g., the console 1200, the console 1200', the RJ 103, the probe portion 104, etc.). Those skilled in the art will appreciate that the light source 101, the RJ 103, the MCU 140, the spectrometer 111, the spectrometer 111 (one or more components thereof) and/or one or more other elements of the system 100, may operate in the same or similar fashion to those like-numbered elements of one or more other systems, such as, but not limited to, the system 100', the system 100", the system 100'", the system 100"", the system 100'"", the system 100"""", the system 100'"""", etc. as discussed herein. Those skilled in the art will appreciate that alternative embodiments of the system 100, the system 100', the system 100", the system 100'", the system 100"", the system 100'"", the system 100"""", the system 100'"""", etc., and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100, the system 100', the system 100", the system 100'", the system 100"", the system 100'"", the system 100"""", and the system 100'"""" as discussed herein, there are similarities. Likewise, while the console or computer 1200 may be used in one or more systems (e.g., the system 100, the system 100', the system 100", the system 100''', the system 100'''', the system 100''''', the system 100'''''', the system 100''''''', etc.), one or more other consoles or computers, such as the console or computer 1200', the processing circuit 1101 or the processing circuit 142, may be used additionally or alternatively.

There are many ways to compute intensity, viscosity, resolution (including increasing resolution of one or more images), creation of color images or any other measurement discussed herein, digital as well as analog. In at least one embodiment, a computer, such as the console or computer 1200, 1200', may be dedicated to control and monitor the SEE devices, systems, methods and/or storage mediums described herein.

Figure 34:
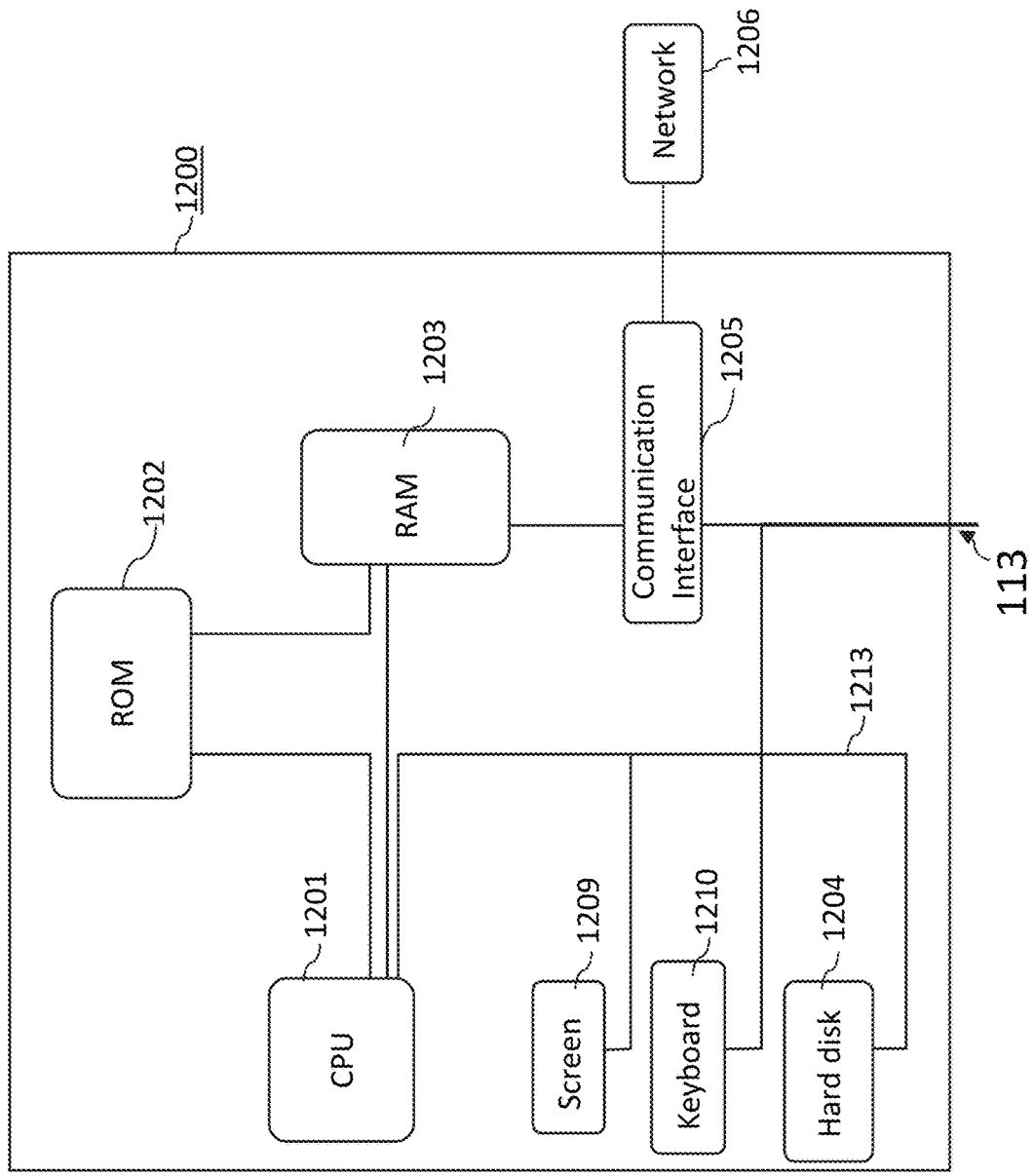
FIG. 34 shows a schematic diagram of an embodiment of a computer that may be used with one or more embodiments of a SEE apparatus or system or an imaging system or one or more methods discussed herein in accordance with one or more aspects of the present disclosure.

Various components of a computer system 1200 (see e.g., the console or computer 1200 as shown in FIGS. 1B-1C) are provided in FIG. 34. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 34). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a SEE device or system, such as, but not limited to, the system 100, the system 100', the system 100", the system 100''', the system 100'''', the system 100''''', the system 100'''''', the system 100''''''', etc., discussed herein above, via one or more lines 1213), and one or more other computer systems 1200 may include one or more combinations of the other aforementioned components (e.g., the one or more lines 1213 of the computer 1200 may connect to other components via line 113 (as diagrammatically shown in FIGS. 1B-1C)). The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for SEE tissue characterization, diagnosis, evaluation and imaging. The system 1200 may further include one or more processors connected via a network connection (e.g., via network 1206). The CPU 1201 and any additional processor being used by the system 1200 may be located in the same telecom network or in different telecom networks (e.g., performing SEE technique(s) may be controlled remotely).

Figure 35:
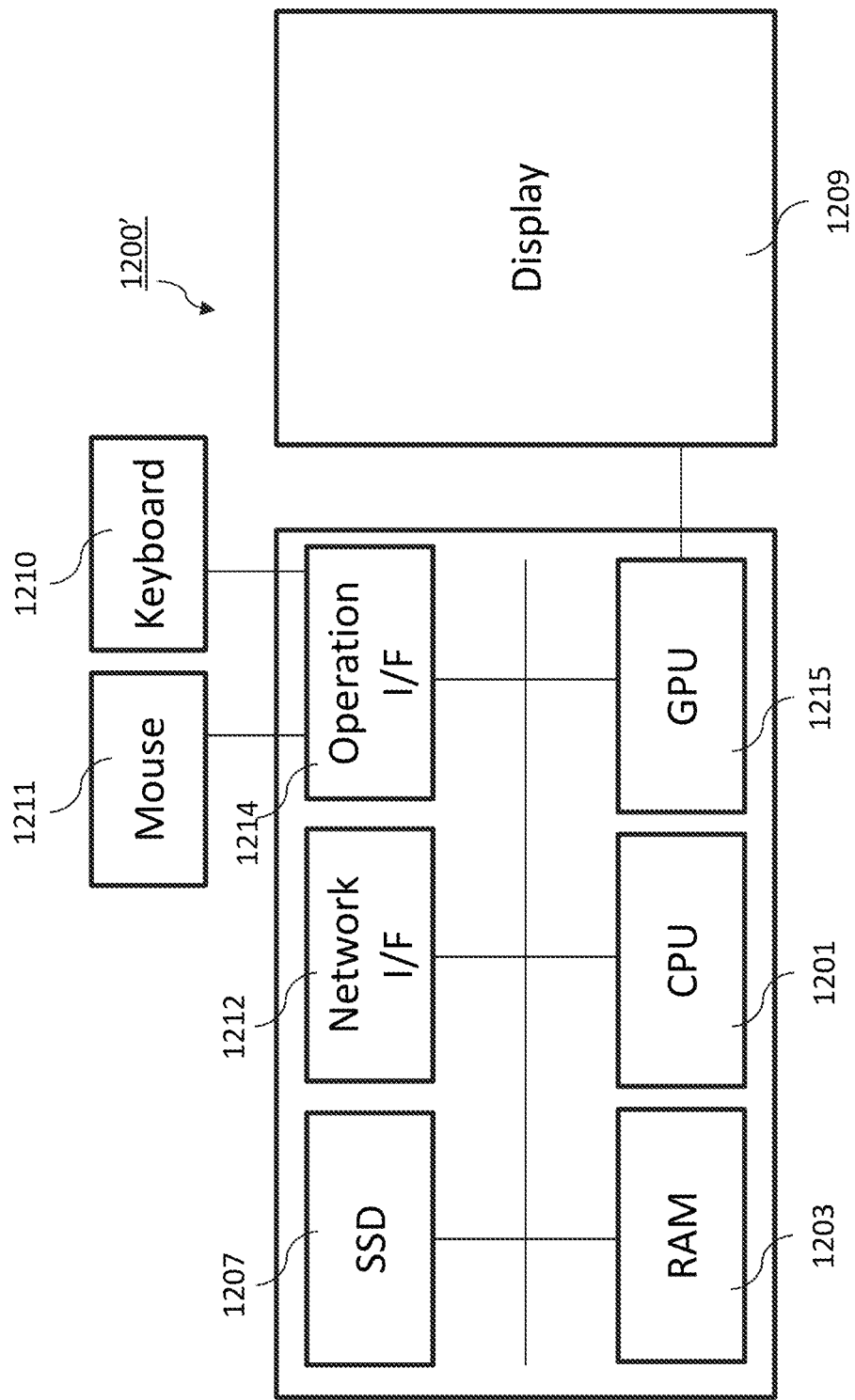
FIG. 35 shows a schematic diagram of another embodiment of a computer that may be used with one or more embodiments of a SEE apparatus or system or an imaging system or methods discussed herein in accordance with one or more aspects of the present disclosure.

The I/O or communication interface 1205 provides communication interfaces to input and output devices, which may include the light source 101, a spectrometer (e.g., the spectrometer 111 (e.g., the communication interface of the computer 1200 may connect to other components via line 113 (as diagrammatically shown in FIGS. 1B-1C and 34))), a microphone, a communication cable and a network (either wired or wireless), a keyboard 1210, a mouse (see e.g., the mouse 1211 as shown in FIG. 35), a touch screen or screen 1209, a light pen and so on. The Monitor interface or screen 1209 provides communication interfaces thereto.

Any methods and/or data of the present disclosure, such as the methods for performing SEE tissue characterization, diagnosis, examination and/or imaging (including, but not limited to, increasing image resolution, obtaining improved black and white images and/or improved color images, etc.) with as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 35), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, the processor of the computer 1200', the image processing unit 142, the image processing unit 1101, etc., as described above may be achieved utilizing suitable hardware, such as that illustrated in the figures. Functionality of one or more aspects of the present disclosure may be achieved utilizing suitable hardware, such as that illustrated in FIG. 34. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG.

10) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 35. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with various components, such as the MCU 140, the motor 1106 and the spectrometer 111, etc., via the operation interface 1214 or the network interface 1212 (e.g., via a cable or fiber, such as the cable or fiber 113 as similarly shown in FIGS. 1B-1C). A computer, such as the computer 1200', may include the MCU 140 and/or the motor 1106 in one or more embodiments. The operation interface 1214 is connected with an operation unit such as a mouse device 1211, a keyboard 1210 or a touch panel device. The computer 1200' may include two or more of each component.

At least one computer program is stored in the SSD 1207, and the CPU 1201 loads the at least one program onto the RAM 1203, and executes the instructions in the at least one program to perform one or more processes described herein, as well as the basic input, output, calculation, memory writing and memory reading processes.

The computer, such as the computer 1200, 1200', the processing unit 142, the processing unit 1101, etc., communicates with the MCU 140 and/or the motor 1106 to perform imaging, and reconstructs an image from the acquired intensity data. The monitor or display 1209, the monitor 1104, etc. displays the reconstructed image, and may display other information about the imaging condition or about an object to be imaged. The monitor 1209/1104 also provides a graphical user interface for a user to operate a SEE system (e.g., the system 100, the system 100', the system 100", the system 100''', the system 100'''', the system 100''''', the system 100'''''', the system 100''''''', etc.). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", the system 100''', the system 100'''', the system 100''''', the system 100'''''', the system 100''''''', etc.) to set or change the imaging condition (e.g., improving resolution of an image or images), and to start or end the imaging. The laser source 101 and the spectrometer 111 may have interfaces to communicate with the computers 1200, 1200' to send and receive the status information and the control signals.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7,551,293; 7,796,270; 7,859,679; 8,045,177; 8,145,018; 8,838,213; 9,254,089; 9,295,391; 9,415,550; and 9,557,154 and arrangements and methods of facilitating photoluminescence imaging, such as those disclosed in U.S. Pat. No. 7,889,348 to Tearney et al. Other exemplary SEE systems are described, for example, in U.S. Pat. Pubs. 2016/0341951; 2016/0349417; US2017/0035281; 2017/167861; 2017/0168232; 2017/0176736; 2017/0290492; 2017/0322079, 2012/0101374; and WO2015/116951; WO2015/116939; WO2017/117203; WO2017/024145; WO2017/165511; WO2017/139657 and U.S. Non-Provisional patent application Ser. No. 15/418,329 filed Jan. 27, 2017, each of which patents, patent publications and patent application(s) are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A two-dimensional image acquiring apparatus comprising:
   a Spectrally Encoded Endoscopy ("SEE") probe including at least one diffractive element and one or more optical fibers, the at least one diffractive element operating to separate and diffract a transmitted light into a first plurality of light fluxes of different wavelength bands such that the diffracted light beams are completely overlapped or completely superposed or substantially overlapped or substantially superposed on a target region;
   a diffraction grating configured to receive a light and to disperse or emit the received light into or as a second plurality of light fluxes of different wavelength bands;
   at least one image sensor or detector that operates to acquire one or more intensities or spectral information from the received light; and
   at least one imaging optical system that operates to image the plurality of light fluxes dispersed or emitted from the received light,
   wherein the diffraction grating, the at least one imaging optical system, and the at least one image sensor or detector are disposed for each of the second plurality of light fluxes dispersed or emitted from the received light to acquire spectral data of each of the plurality of light fluxes, and
   wherein the at least one diffractive element operates to rotate such that an image of the at least one image sensor or detector is changed, and a two-dimensional image is acquired from the image.

2. The image acquiring apparatus of claim 1, further comprising a light source that operates to transmit the transmitted light to the SEE probe via at least one of the one or more optical fibers such that:
   (i) the at least one diffractive element is irradiated with the transmitted light;
   (ii) a sample or a target located in the target region is irradiated with the diffracted light fluxes of different wavelength bands; and
   (iii) reflected scattered light from the sample or the target is detected by the at least one image sensor or detector.

3. The image acquiring apparatus of claim 2, wherein the light source is a supercontinuum (SC) light source having a wavelength band from blue to infrared.

4. The image acquiring apparatus of claim 1, further comprising an optical branching part that operates to branch the transmitted light into at least two or more, wherein the branched light is input to a single collimator lens and imaged as a plurality of spectral sequences by the imaging optical system, the plurality of spectral sequences are each individually detected by the at least one image sensor or detector, and at the time of the at least one image sensor or detector detecting the plurality of spectral sequences, signal positions each detected independently are relatively shifted.

5. The image acquisition apparatus according to claim 4, wherein the number of the at least one image sensor or detector is plural and matches the number of optical branches.

6. The image acquisition apparatus according to claim 5, wherein each of the plurality of image sensors or detectors is shifted from each other in a direction parallel to a direction in which wavelengths of the spectral sequences are arrayed.

7. The image acquisition apparatus according to claim 4, wherein the at least one image sensor or detector is a single two-dimensional imaging device, with the plurality of spectral sequences being imaged on the two-dimensional imaging device at different positions in a direction orthogonal to a direction in which wavelengths of the spectral sequences are arrayed.

8. The image acquisition apparatus according to claim 7, wherein fiber end faces of fibers of the one or more optical fibers that perform transmission are shifted so the plurality of spectral sequences are imaged at positions on the two-dimensional imaging device shifted from each other in a direction parallel to a direction in which wavelengths of the spectral sequences are arrayed.

9. The image acquisition apparatus according to claim 4, wherein at least one of:
   (i) a plurality of the one or more optical fibers are used as detection fibers to transmit the received light, and the detection fibers are formed as at least one fiber bundle where a plurality of optical fibers have been bundled;
   (ii) the optical branching part branches or includes the at least one fiber bundle as a plurality of small bundles; and/or
   (iii) the at least one fiber bundle has one end positioned around the diffraction grating, and fibers that have been positioned adjacently are connected to or included in different small bundles.

10. The image acquiring apparatus of claim 1, wherein at least one of:
   (i) the at least one image sensor or detector is disposed at or near a focal point of the imaging optical system; and/or
   (ii) the image acquiring apparatus is an endoscope apparatus.

11. The image acquiring apparatus of claim 1, further comprising:
   a collimator configured to form a light flux emitted from the received light via at least one of the one or more optical fibers into a parallel light flux; and
   a light flux splitter configured to split the parallel light flux emitted by the collimator into the second plurality of light fluxes, the angle of travel of each light flux of the second plurality of light fluxes being different,
   wherein the diffraction grating operates to emit each of the second plurality of light fluxes received from the light flux splitter at a different angle according to a wavelength of each of the second plurality of light fluxes; and
   the light flux splitter operates such that the second plurality of light fluxes are overlaid at an incident pupil of the at least one imaging optical system.

12. The image acquiring apparatus of claim 11, wherein the light flux splitter is made up of a plurality of reflecting faces having different normal line angles.

13. The image acquiring apparatus of claim 1, wherein at least one of:
   (i) the at least one image sensor or detector comprises a plurality of line sensors, and each of the plurality of line sensors is disposed to detect light of a different wavelength according to pixels; and/or
   (ii) the image acquiring apparatus further comprises at least one processor that operates to add output of pixels of the plurality of line sensors that correspond to a same wavelength.

14. The image acquiring apparatus of claim 1, wherein at least one of:
   (i) the at least one image sensor or detector comprises an area sensor; and/or
   (ii) the image acquiring apparatus further comprises at least one processor that operates to add output of pixels of the area sensor that correspond to a same wavelength.

15. The image acquiring apparatus of claim 1, further comprising at least one wavelength band splitting element that splits the light that has been transmitted into a plurality of wavelength bands,
   wherein luminous fluxes that have been split with the wavelength band splitting element are incident on the imaging optical system at different angles, and
   wherein the luminous fluxes that have been spectrally dispersed per wavelength with the diffraction grating are formed on the at least one image sensor or detector into an image that has a reduced or minimal gap or has no gap in a spectrally dispersed direction.

16. The image acquiring apparatus of claim 15, wherein the at least one wavelength band splitting element is disposed at a portion prior to the diffraction grating, and
   wherein the luminous fluxes that have been split by the at least one wavelength band splitting element are made to enter the diffraction grating at different angles.

17. The image acquiring apparatus of claim 16, wherein the angles at which the luminous fluxes that have been split by the at least one wavelength band splitting element enter the diffraction grating are selected so that a maximum value of the diffraction efficiency of the diffraction grating is positioned in the wavelength bands that have been split.

18. The image acquiring apparatus of claim 15, wherein the wavelength bands that are split by the at least one wavelength band splitting element are between a wavelength band corresponding to a red signal in a color image and a wavelength band corresponding to a green signal in the color image.

19. The image acquiring apparatus of claim 15, wherein at least one of:
  (i) in the wavelength bands split by the at least one wavelength band splitting element, a specific wavelength band not used by the image acquiring apparatus is not incident on the at least one image sensor or detector;
  (ii) the at least one wavelength band splitting element is a dichroic mirror;
  (iii) an angle at which the wavelength band corresponding to a red signal enters the diffraction grating is larger than an angle at which the wavelength band corresponding to a blue and green signal enters the diffraction grating; and/or
  (iv) a wavelength region corresponding to the red signal is within a range of 640 nm to 800 nm, and a wavelength region corresponding to the blue and green signal is within a range of 400 nm to 590 nm.

20. The image acquiring apparatus of claim 1, further comprising at least one of:
  (i) at least one processor that operates to receive one or more electric signals from the at least one sensor or detector and to generate the two-dimensional image;
  (ii) a display or a screen that operates to display the generated, two-dimensional image;
  (iii) a spacer element disposed at a distal end of the SEE probe such that the spacer element and the at least one diffractive element are adjacent and/or connected;
  (iv) a gradient-index lens disposed in the SEE probe adjacent or connected to the spacer element;
  (v) a motor and/or a rotary junction that operates to rotate to the SEE probe;
  (vi) a motion control component that operates to change a speed of the motor and/or the rotary junction; and/or
  (vii) a sheath housing the SEE probe.

21. The image acquiring apparatus of claim 1, wherein the one or more optical fibers include: (i) one or more illumination fibers that operate to send light from a light source to the at least one diffractive element to illuminate the target region with light; and (ii) one or more detection fibers that operate to receive light reflected from a target or a sample disposed in the target region and that passes back through the at least one diffractive element and into the one or more detection fibers.

* * * * *